US011324452B2

(12) United States Patent
Sayani et al.

(10) Patent No.: US 11,324,452 B2
(45) Date of Patent: *May 10, 2022

(54) ANATOMICAL-IMAGING COMMUNICATION DEVICE

(71) Applicant: The Aga Khan University, Karachi (PK)

(72) Inventors: Saleem Sayani, Wynnewood, PA (US); Muhammad Abdul Muqeet, Karachi (PK); Hafiz Imtiaz Ahmed, Karachi (PK)

(73) Assignee: The Aga Khan University, Karachi (PK)

( * ) Notice: Subject to any disclaimer, the term of this patent is extended or adjusted under 35 U.S.C. 154(b) by 0 days.

This patent is subject to a terminal disclaimer.

(21) Appl. No.: 17/146,860

(22) Filed: Jan. 12, 2021

(65) Prior Publication Data

US 2021/0128066 A1 May 6, 2021

Related U.S. Application Data

(63) Continuation of application No. 16/672,367, filed on Nov. 1, 2019, now Pat. No. 10,918,338, which is a
(Continued)

(30) Foreign Application Priority Data

Jan. 12, 2018 (PK) ...................... 24/2018

(51) Int. Cl.
*G16H 30/20* (2018.01)
*A61B 5/00* (2006.01)
(Continued)

(52) U.S. Cl.
CPC ........ *A61B 5/6898* (2013.01); *A61B 1/00016* (2013.01); *A61B 1/042* (2013.01);
(Continued)

(58) Field of Classification Search
CPC ..... A61B 5/6898; A61B 1/00016; A61B 3/13; A61B 1/042; A61B 5/0077; A61B 1/227;
(Continued)

(56) References Cited

U.S. PATENT DOCUMENTS 7,369,692 B2 * 5/2008 Shirai .................... A61B 5/442
382/128
7,986,342 B2 * 7/2011 Yogesan ................ A61B 5/441
600/101
(Continued)

FOREIGN PATENT DOCUMENTS

| CN | 203677125 | 7/2014 |
| JP | H1019858 | 1/1998 |

(Continued)

OTHER PUBLICATIONS

"All Products." Firefly, 2015, 3 pages. Web. Feb. 23, 2018, http://fireflyglobal.com/all-prodoct/#healthcare.
(Continued)

*Primary Examiner* — John R Schnurr
(74) *Attorney, Agent, or Firm* — Fish & Richardson P.C.

(57) ABSTRACT

A device is described that can include a probe, a mobile device, and at least one processor. The probe can examine a corresponding anatomical part of a body. The mobile device can have a camera to take an image of the anatomical part of the body. The mobile device can execute a patient-application to process the image. The at least one processor can be configured to transmit the processed image to a server via a communication network. Related apparatuses, systems, methods, techniques and articles are also described.

19 Claims, 18 Drawing Sheets

Related U.S. Application Data continuation of application No. 15/905,077, filed on Feb. 26, 2018, now Pat. No. 10,463,307.

(51) Int. Cl.

| | |
|---|---|
| *G06T 5/20* | (2006.01) |
| *G06F 3/0482* | (2013.01) |
| *A61B 1/227* | (2006.01) |
| *A61B 1/233* | (2006.01) |
| *A61B 1/24* | (2006.01) |
| *A61B 3/14* | (2006.01) |
| *A61B 1/00* | (2006.01) |
| *A61B 3/13* | (2006.01) |
| *A61B 1/04* | (2006.01) |

(52) U.S. Cl.
CPC .............. *A61B 1/227* (2013.01); *A61B 1/233* (2013.01); *A61B 1/24* (2013.01); *A61B 3/13* (2013.01); *A61B 3/14* (2013.01); *A61B 5/0013* (2013.01); *A61B 5/0022* (2013.01); *A61B 5/0077* (2013.01); *A61B 5/441* (2013.01); *A61B 5/7435* (2013.01); *A61B 5/7475* (2013.01); *G06F 3/0482* (2013.01); *G06T 5/20* (2013.01); *G16H 30/20* (2018.01); *A61B 1/00105* (2013.01); *A61B 5/0088* (2013.01); *G06T 2200/24* (2013.01); *G06T 2210/41* (2013.01)

(58) Field of Classification Search
CPC .. A61B 1/233; A61B 1/24; A61B 3/14; A61B 5/441; A61B 5/0022; A61B 5/0013; A61B 5/7435; A61B 5/7475; A61B 5/0088; A61B 1/00105; G06T 5/20; G06T 2200/24; G06T 2210/41; G06F 3/0482; G16H 30/20; G16H 10/60; G16H 30/40; G16H 40/63

See application file for complete search history.

(56) References Cited

U.S. PATENT DOCUMENTS

| | | | | |
|---|---|---|---|---|
| 10,188,294 | B2 | 1/2019 | Myung et al. | |
| 2009/0319897 | A1* | 12/2009 | Kotler | H04N 1/6013 |
| | | | | 715/838 |
| 2012/0245422 | A1* | 9/2012 | Hasbun | G06F 1/1656 |
| | | | | 600/200 |
| 2012/0320340 | A1* | 12/2012 | Coleman, III | A61B 3/10 |
| | | | | 351/208 |
| 2013/0083183 | A1* | 4/2013 | Cheng | A61B 1/227 |
| | | | | 362/268 |
| 2013/0083185 | A1* | 4/2013 | Coleman, III | A61B 3/14 |
| | | | | 348/78 |
| 2013/0226993 | A1* | 8/2013 | Dorey | G06F 16/95 |
| | | | | 709/203 |
| 2016/0106369 | A1* | 4/2016 | Yetik | G02B 21/362 |
| | | | | 600/476 |
| 2016/0367135 | A1* | 12/2016 | Myung | A61B 3/1208 |
| 2018/0158211 | A1* | 6/2018 | Ghazizadeh | G16H 30/40 |
| 2018/0349008 | A1* | 12/2018 | Manzari | H04N 5/247 |
| 2019/0038260 | A1* | 2/2019 | Lee | A61B 8/54 |
| 2019/0066832 | A1* | 2/2019 | Kang | A61B 5/4884 |
| 2019/0216402 | A1* | 7/2019 | Sayani | A61B 5/6898 |

FOREIGN PATENT DOCUMENTS

| | | |
|---|---|---|
| JP | 2011183056 | 9/2011 |
| WO | WO0106924 | 2/2001 |
| WO | WO2012065163 | 5/2012 |

OTHER PUBLICATIONS

Cellscope—Building Smart Mobile Tools for Better Family Health. CellScope, 2018, 5 pages. Web. Feb. 23, 2018. https://www.cellscope.com/.

D-Eye Smartphone-Based Retinal Screening System. D-Eye Srl, 2016. 4 pages. Web. Feb. 23, 2018. (https://www.d-eyecare.com/).

Dino-Lite Digital Microscope: The Industry Standard. Dino-Lite Europe/IDCP B.V, 2015, pp. 1-68. Web. Feb. 23, 2018. (http://www.dino-lite.eu/index.php/en/products/medical).

Examination Report from PK Application No. 24/2018, dated Jun. 14, 2019, 2 pages.

Get HUD. HUD, 2014. 4 pages. Web. Feb. 23, 2018. http://www.firsthud.com/#meethud.

Riester 3970 Ri-Screen® Medical Camera. Tiger Medical, Inc., 2018, 2 pages. Web. Feb. 23, 2018. https://www.tigermedical.com/Products/Ri-screen-Medical-Camera RIE3970.aspx.

* cited by examiner

ANATOMICAL-IMAGING COMMUNICATION DEVICE

CROSS-REFERENCE TO RELATED APPLICATIONS

This is a continuation of U.S. application Ser. No. 16/672,367, filed on Nov. 1, 2019, which is a continuation of U.S. application Ser. No. 15/905,077, filed on Feb. 26, 2018 (now U.S. Pat. No. 10,463,307), which claims priority to Pakistan Patent Application No. 24/2018, filed on Jan. 12, 2018. The contents of each of the documents noted above are hereby fully incorporated by reference in their entireties.

TECHNICAL FIELD

The subject matter described herein relates to an anatomical-imaging communication device that can: be calibrated to image an anatomical region of a body, image the anatomical region to obtain one or more images, filter the one or more images, and transmit the one or more filtered images to a clinical computer via a communication network.

BACKGROUND

Screening and examining of anatomical regions of interest on the human body—such as skin, eye, nose, throat, ear, teeth and mouth—are conventionally performed using different diagnostic devices rather than a single device. For example, a dermascope, an otoscope, an ophthalmoscope, an otolaryngoscope, and a dental scope are used for examining skin, ear, eyes, ENT (i.e., ear, nose and throat), teeth, and mouth, respectively. Such traditional devices are large and bulky. Moreover, they often lack the capability to document (e.g., image) regions of interest, as a result of which patient electronic health records may not be regularly updated and maintained. Further, traditional devices lack simplicity of structure/construction, as a result of which training on and troubleshooting of such devices is time consuming and tedious.

SUMMARY

In one aspect, a device is described that can include a probe, a mobile device, and at least one processor. The probe can examine a corresponding anatomical part of a body. The mobile device can have a camera to take an image of the anatomical part of the body. The mobile device can execute a patient-application to process the image. The at least one processor can be configured to transmit the processed image to a server via a communication network.

In some variations, one or more of the following can be implemented either individually or in any feasible combination. The anatomical part of the body can be one of an ear, a nose, an eye, a mouth, teeth, and skin. The at least one processor can be a part of the mobile device. The server can be a cloud computing server. The server can be configured to send the processed image to a clinician-application. The device can further include at least one lens that is positioned between the camera and the anatomical region.

In another aspect, a cloud computing server is described that can include: at least one of one or more software development kits (SDKs) and one or more web modules, an application programming interface (API), and at least one controller. The at least one of one or more SDKs and one or more web modules can receive an image of an anatomical part of a body from a patient-application executed on a mobile device within a device. The API can enable at least one processor to read the image. The at least one controller can include at least one processor. The at least one processor can be configured to: display a plurality of filters on a graphical user interface of the patient-application; receive, from the graphical user interface, an input on the graphical user interface comprising a filter selected from the plurality of filters; identify at least one parameter of a plurality of parameters that is associated with and specific to the selected filter; execute the selected filter on the image by using the at least one parameter to generate a filtered image; and transmit the filtered image to the a clinician application via a communication network.

In some variations, one or more of the following can be implemented either individually or in any feasible combination. The at least one processor can calibrate the mobile device prior to the receiving of the image. The calibrating of the mobile device can include: receiving a prior image of the anatomical part from the mobile device; and executing a plurality of functions on the prior image to return the plurality of parameters for the mobile device, the at least one parameter of the plurality of parameters being used to filter the image. The plurality of functions can include two or more of a morphological operation on the prior image, a histogram equalization function on the prior image, a noise removal function on the prior image, a contrast adjustment function on the prior image, an unsharp masking function on the prior image. The cloud computing server can further include at least one database to store the plurality of parameters.

In yet another aspect, a system is described that can include a device and a server. The device can include: a probe to examine a corresponding anatomical part of a body; a mobile device having a camera to take an image of the anatomical part of the body, the mobile device executing a patient-application to process the image; and at least one first processor configured to transmit the processed image to a server via a communication network. The server can include: at least one of one or more software development kits and one or more web modules to receive the processed image of the anatomical part from the at least one first processor; an application programming interface to enable at least one second processor to read the processed image; and at least one controller including the at least one second processor. The at least one second processor can be configured to: display a plurality of filters on a graphical user interface of the patient-application; receive, from the graphical user interface, an input on the graphical user interface comprising a filter selected from the plurality of filters; identifying at least one parameter of a plurality of parameters that is associated with and specific to the selected filter; executing the selected filter on the processed image by using the at least one parameter to generate a filtered image; and transmitting the filtered image to the a clinician application via a communication network.

In some variations, one or more of the following can be implemented either individually or in any feasible combination. The anatomical part of the body can be one of an ear, a nose, an eye, a mouth, teeth, and skin. The at least one first processor can be a part of the mobile device. The system can further include at least one lens that is positioned between the camera of the mobile device and the anatomical region. The at least one second processor can calibrate the mobile device prior to the receiving of the image. The calibrating of the mobile device can include: receiving a prior image of the anatomical part from the mobile device; and executing a plurality of functions on the prior image to return the plurality of parameters for the mobile device, the at least one parameter of the plurality of parameters being used to filter the image. The plurality of functions can include a morphological operation, a histogram equalization function, a noise removal function, a contrast adjustment function, and an unsharp masking function. The cloud computing server can further include at least one database to store the plurality of parameters.

The subject matter described herein provides many advantages. For example, a single device can be used to screen and examine various anatomical regions of interest on the human body, such as skin, eye, nose, throat, ear, teeth, mouth, and the like. This device can be small, light in weight, and easy to carry. The device can document (e.g., image) the anatomical regions of interest, as a result of which patient electronic health records can be automatically and regularly updated and maintained. The device can have a simple structure/construction, as a result of which training on and troubleshooting of the device is easy, quick, and can be performed by a layman.

The details of one or more variations of the subject matter described herein are set forth in the accompanying drawings and the description below. Other features and advantages of the subject matter described herein will be apparent from the description, the drawings, and the claims.

BRIEF DESCRIPTION OF DRAWINGS

Like reference symbols in the various drawings indicate like elements.

DETAILED DESCRIPTION

Figure 1:
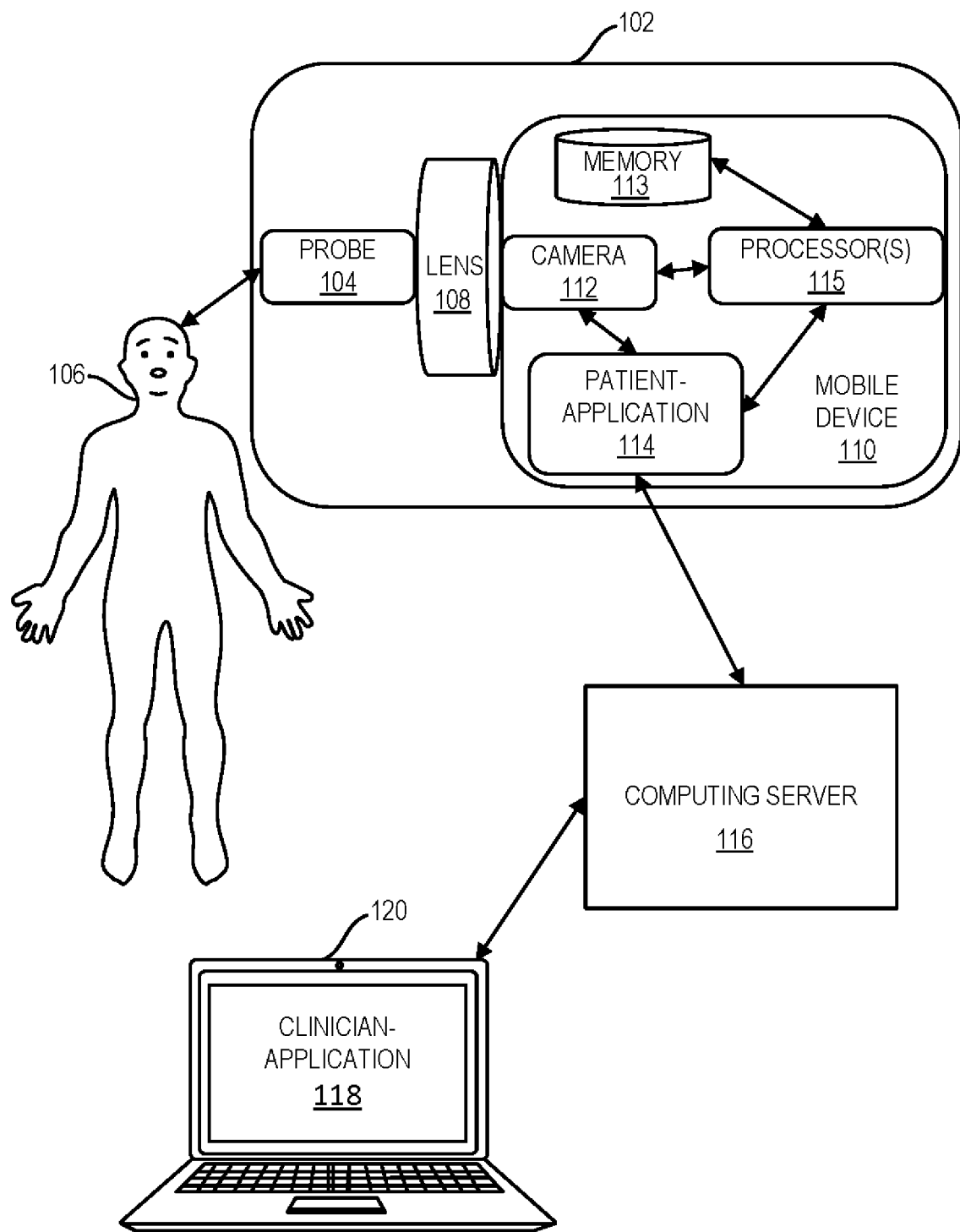
FIG. 1 illustrates an anatomical-imaging communication device (also referred to as the device) that includes a probe, a detachable lens, and a mobile device having a camera to click images of an anatomical region and a patient-application to process the images and transmit the processed images to a clinician-application, in accordance with some implementations of the current subject matter.

FIG. 1 illustrates an anatomical-imaging communication device 102 (also referred to as the device) that includes a probe 104 that is changeable based on anatomical part of a patient 106 to be examined; a detachable lens 108 to view that anatomical part and specific to that anatomical part; and a mobile device (e.g., mobile phone) 110 including a camera 112 to capture the anatomical part, a patient-application 114 that is calibrated using specific filters to capture high quality images, a memory 113 to store the captured images, and a processor/controller 115 that can transmit the images to a computing server 116. The computing server 116, which can serve as the back-end for the patient-application 114 as well as a clinician-application 118, can store the images in a database, and can transmit those images to the clinician-application 118 configured run on a clinical computer 120.

The design of the device 102 can vary based on the anatomical part being examined, as explained by FIGS. 2-5. Some aspects of the design are further clarified by FIGS. 6-9. One example of the computing server 116 is described below by FIG. 10. The calibration of the mobile device 110 is discussed below by FIGS. 11-13. The use of the calibrated mobile device 110 is explained below by FIGS. 14-16. One example of a graphical user interface of the clinician-application 118 is described below by FIG. 17. Another alternative device 102 is presented below by FIG. 18.

The probe 104 can vary based on the anatomical part being examined. For example, the probe 104 can be one or more of: an otoscope probe, an optoscope probe, and a dermascope probe that can be extended to form a dental probe. The otoscope probe is described in more detail below by FIG. 2. The optoscope probe is discussed in more detail below by FIG. 3. The dermascope probe is described in further detail below by FIG. 4. The dental scope probe is discussed in more detail below by FIG. 5. Although an otoscope probe, an optoscope probe, a dermascope probe, and a dental probe are described, in alternate implementations, any other probe can be used.

The lens 108 can be a convex lens that can have a diameter between 16 mm and 23 mm.

The mobile device 110 can be a cellular smart phone, a tablet computer, a phablet computer, or the like. The mobile device 110 can be light in weight so that the device 102 remains light in weight, portable, and easy to use. The camera 112 can include: a lens (which may be separate from the lens 108), which can enable the camera to see the anatomical region; a converter, which can convert the output of the lens into digital data; and at least one processor (which may be separate from the processor 115), which can process the digital data—e.g., apply image processing algorithms such as JPEG optimization and color correction—by implementing and transition that processed data into an image file. In one implementation, the camera 112 can have a resolution of two or more megapixels. In an alternate implementation, the camera 112 can have any value of resolution.

While the mobile device 110 is described as including a camera 112, in alternate implementations the mobile device 110 and the camera 112 can be separate physical entities that are communicatively coupled with each other via, for example, a wired or a wireless connection.

The patient-application 114 can be a software application executed on the mobile device 110, which can have an iPhone operating system (IOS), ANDROID, or any other operating system.

The computing server 116 can be a device or a computer program that can provide functionality for devices or other programs or devices, which can be referred to as clients. The computing server 116 can be a cloud computing server, as explained below by FIG. 8. In an alternate implementation, the computing server 116 can be a cluster of computers. In another implementation, the computing server 116 can be one or more of: a desktop computer, a laptop computer, a tablet computer, a phablet computer, a cellular/smart phone, and any other suitable computing device. The computing server 116 can be communicatively coupled with the mobile device 110 via a communication network, such as one or more of: local area network, internet, wide area network, metropolitan area network, BLUETOOTH network, infrared network, wired network, and any other communication network.

The clinician-application 118 can be a software application executed on the clinical computer 120, which can have a WINDOWS, LINUX, MAC OS, iPhone operating system (IOS), ANDROID, or any other operating system.

The clinical computer 120 can be one or more of: a desktop computer, a laptop computer, a tablet computer, a phablet computer, a cellular/smart phone, and any other suitable computing device. The clinical computer 120 can be communicatively coupled with the computing server 116 via a communication network, such as one or more of: local area network, internet, wide area network, metropolitan area network, BLUETOOTH network, infrared network, wired network, and any other communication network.

Figure 2:
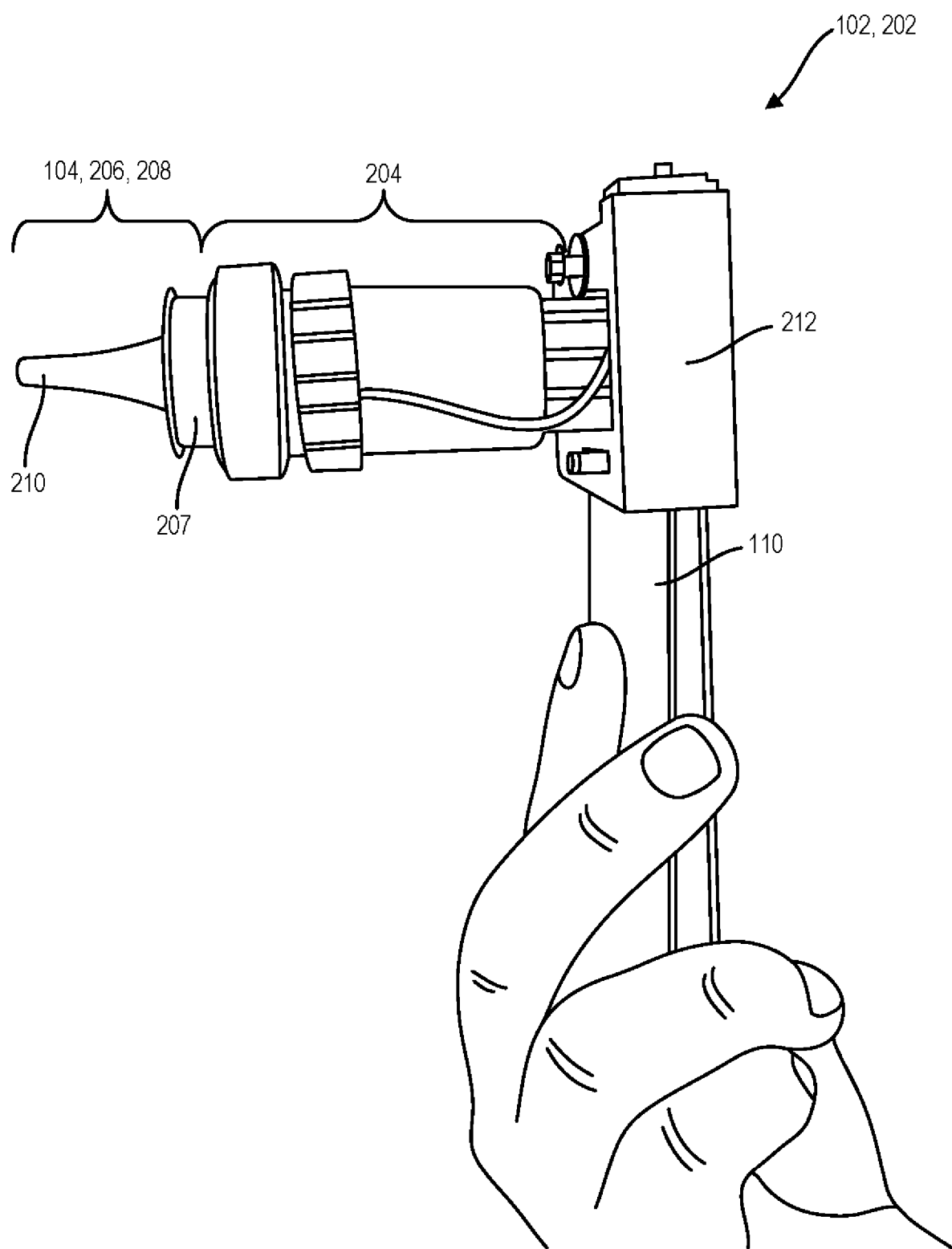
FIG. 2 illustrates a design of the device when the device is being used as an otoscope to examine an ear of the patient, in accordance with some implementations of the current subject matter.

FIG. 2 illustrates a design of the device 102 when the device 102 is being used as an otoscope 202 to examine an ear of the patient 106. The otoscope 202 can include a probe 104, a lens-holder 204 configured to securely hold a lens 108, and a mobile device 110. The probe 104 here is an otoscope probe 206, which can include an ear-piece holder 207 that can securely hold an otoscope head 208. Aspects of the ear-piece holder 207 are described below by FIG. 7. The otoscope head 208 can have a height of 13.624 mm, an internal diameter of 36.576 mm, a thickness of 2.622 mm, and an aperture of 22.860 mm. The otoscope head 208 can have an attachment feature that can allow the otoscope probe 206 to be attached or fixed to the lens-holder 204.

The otoscope head 208 can include two protrusions 210 opposite each other (note only one protrusion is shown, as the other protrusion is hidden) such that one of the protrusions 210 is configured to interface with the ear of the patient 106. While two protrusions 210 are described (i.e., one shown, and the other hidden in the drawing), in alternate implementations the otoscope head 208 can have a single protrusion 210 that is shown in the drawing. Each of the two protrusions 210 can have a thickness of 3.048 mm.

The aperture of the otoscope head 208 head can permit specula of different base diameters—e.g., 25 mm, 27 mm, and 30 mm—to be attached so as to firmly secure the specula being used in place. The specula to be used can be chosen based on the age of the patient—e.g., age less than or equal to 18 years, or more than 18 years—and/or the size of the ear being examined.

The structure of the lens-holder 204 is further described below by FIG. 6. The lens-holder 204 can be securely attached to the mobile device 110 via a gripper part 212, which is described in further detail below by FIG. 9.

Figure 3:
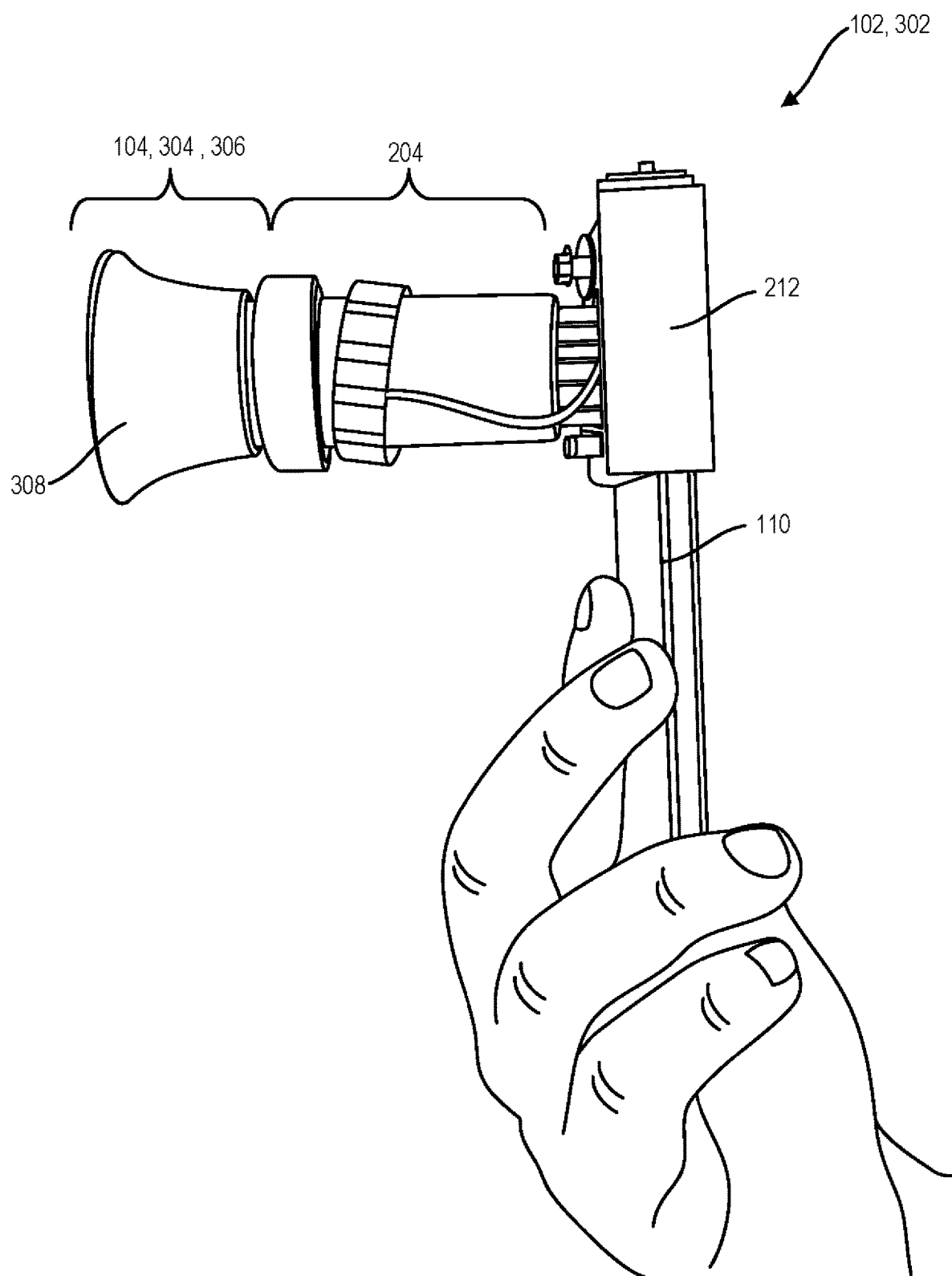
FIG. 3 illustrates a design of the device when the device is being used as an optoscope to examine an eye of the patient, in accordance with some implementations of the current subject matter.

FIG. 3 illustrates a design of the device 102 when the device 102 is being used as an optoscope 302 to examine an eye of the patient 106. The optoscope 302 can include a probe 104, a lens-holder 204 configured to securely hold a lens 108, and a mobile device 110. The probe 104 here is an optoscope probe 304, which can include an optoscope head 306. The optoscope head 306 can include a truncated cone 308 such that the larger base of the truncated cone 308 can interface with the eye of the patient 106.

The optoscope head 306 can have a base portion and an aperture. The total height of the optoscope head 306 can be 18.416 mm, of which the height of the base portion can be 11.078 mm and the height of the aperture can be 7.338 mm. The diameter of the base portion can be 36.107 mm, and the aperture diameter can be 24.618 mm. The aperture can have a thickness of 3.009 mm. The optoscope probe 304 can have an attachment feature that can allow the optoscope probe 304 to be attached or fixed to the lens-holder 204. The truncated cone 308 can be securely placed on the aperture. The truncated cone 308 can be soft and hollow so as to allow the eye to be examined without discomfort to the patient 106. The truncated cone 308 can have a base diameter of 30 mm, an outer diameter of 52 mm, a height of 28 mm, and a thickness of 1.7 mm.

Figure 4:
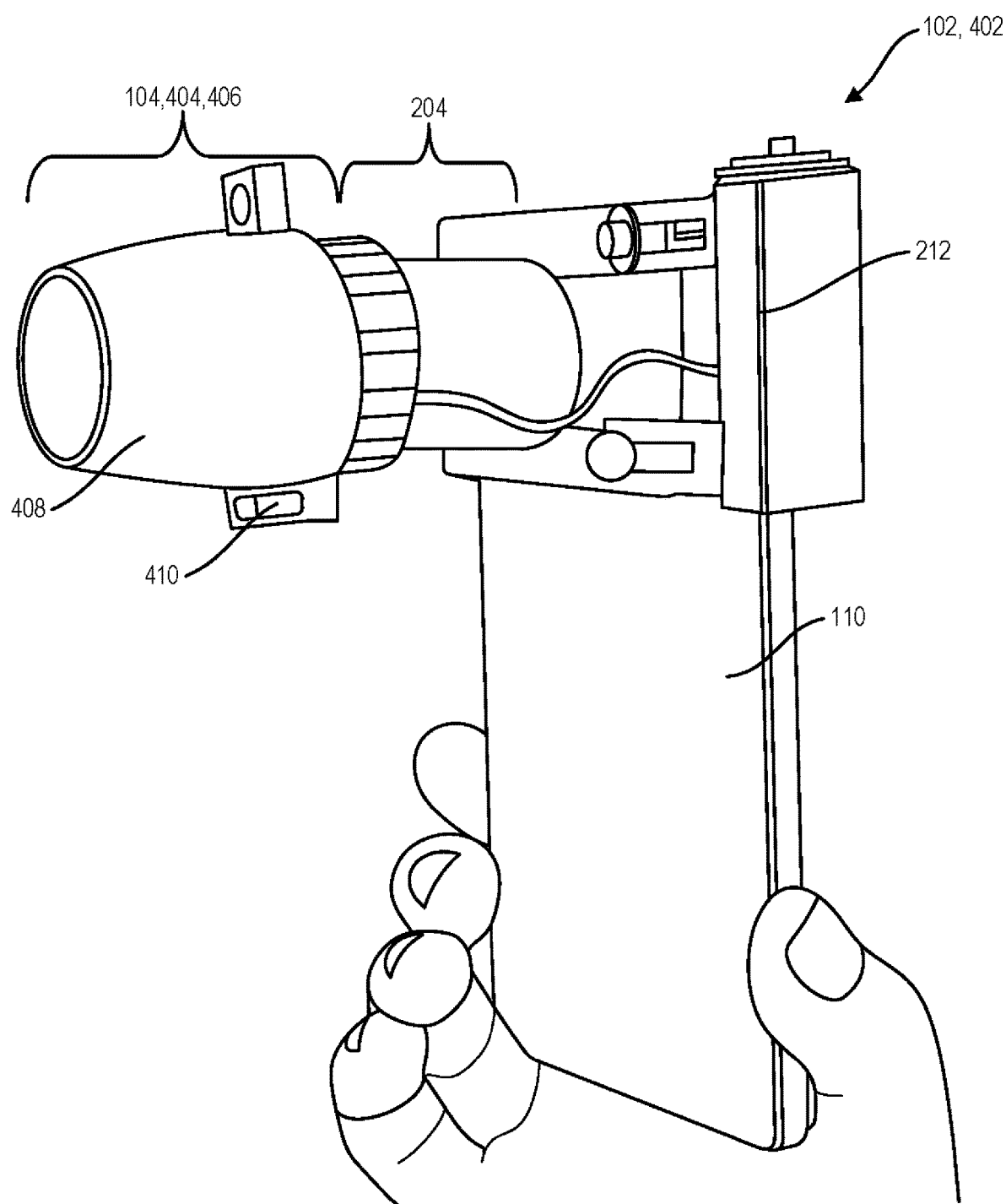
FIG. 4 illustrates a design of the device when the device is being used as a dermascope to examine skin of the patient, in accordance with some implementations of the current subject matter.

FIG. 4 illustrates a design of the device 102 when the device 102 is being used as a dermascope 402 to examine skin of the patient 106. The dermascope 402 can include a probe 104, a lens-holder 204 configured to securely hold a lens 108, and a mobile device 110. The probe 104 here is a dermascope probe 404, which can include a dermascope head 406. The dermascope head 406 can include a base portion and an aperture. The aperture can be a curved truncated cone 408 such that the smaller base of the truncated cone 408 is configured to interface with the skin of the patient 106.

The total height of the dermascope head 406 can be 33.986 mm, of which the height of the base portion can be 9.144 mm and the height of the aperture (i.e., curved truncated cone 408) can be 24.842 mm. The diameter of the base portion can be 36.576 mm. At the point of attachment of the base portion and the aperture (i.e., curved truncated cone 408), both the base portion and the aperture (i.e., curved truncated cone 408) can have a diameter of 36.576 mm. The diameter of the aperture (i.e., curved truncated cone 408) at the top (i.e., the end that is the closest to the skin of the patient 106) can be 26.033 mm. The aperture (i.e., curved truncated cone 408) can have a thickness of 3.048 mm.

Figure 5:
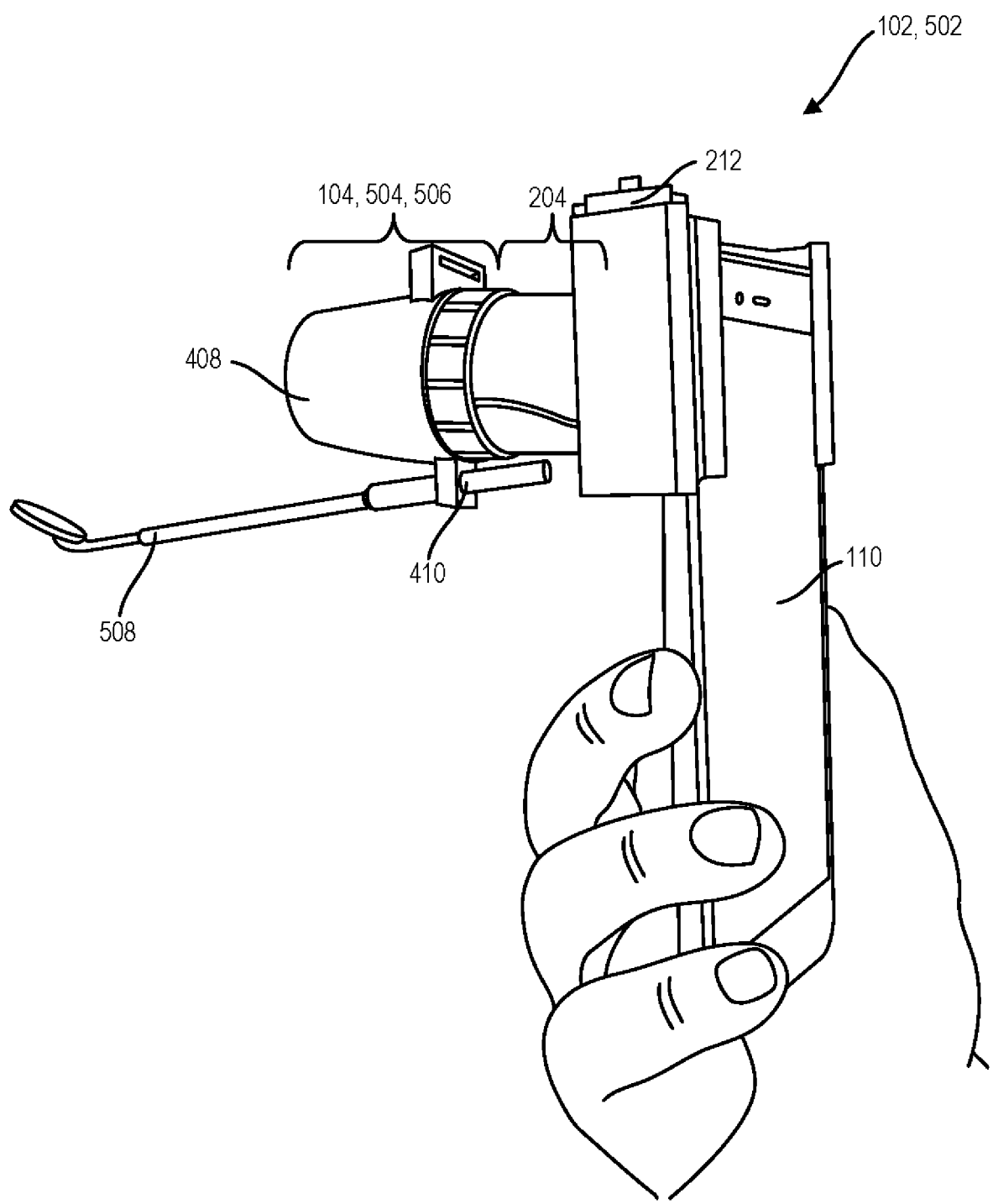
FIG. 5 illustrates a design of the device when the device is being used as a dental scope to examine one or more teeth of the patient, in accordance with some implementations of the current subject matter.

The dermascope head 406 can include one or more protrusions 410 for extending the dermascope 402 into a dental scope of FIG. 5. The one or more protrusions 410 can allow attachment to a tongue depressor and/or a dental mirror so as to convert the dermascope to the dental scope of FIG. 5. For attaching a tongue depressor to the dermascope head, at least one protrusion 410 can have a width of 24.994 mm and a height of 8.932 mm. For attaching a dental mirror, at least one protrusion 410 can have a width of 9.144 mm and a height of 9.144 mm.

FIG. 5 illustrates a design of the device 102 when the device 102 is being used as a dental scope 502 to examine one or more teeth of the patient 106. The dental scope 502 can include a probe 104, a lens-holder 204 configured to securely hold a lens 108, and a mobile device 110. The probe 104 here can be a dental scope probe 504 (which can be same as the dermascope probe 404), which can include a dental scope head 506 (which can be same as the dermascope head 406). The dental scope head 506 can include a base portion and an aperture. The aperture can be a curved truncated cone 408 such that the smaller base of the truncated cone 408 is configured to interface with the teeth of the patient 106.

The total height of the dental scope head 506 can be 33.986 mm, of which the height of the base portion can be 9.144 mm and the height of the aperture (i.e., curved truncated cone 408) can be 24.842 mm. The diameter of the base portion can be 36.576 mm. At the point of attachment of the base portion and the aperture (i.e., curved truncated cone 408), both the base portion and the aperture (i.e., curved truncated cone 408) can have a diameter of 36.576 mm. The diameter of the aperture (i.e., curved truncated cone 408) at the top (i.e., the end that is the closest to the skin of the patient 106) can be 26.033 mm. The aperture (i.e., curved truncated cone 408) can have a thickness of 3.048 mm.

The dental scope head 506 can include one or more protrusions 410 that can allow attachment to a dental mirror 508 and/or a tongue depressor. This way, a dermascope 402 can be easily converted to the dental scope 502. For attaching a tongue depressor to the dental scope head 506, at least one protrusion 410 can have a width of 24.994 mm and a height of 8.932 mm. For attaching a dental mirror to the dental scope head 506, at least one protrusion 410 can have a width of 9.144 mm and a height of 9.144 mm.

Figure 6:
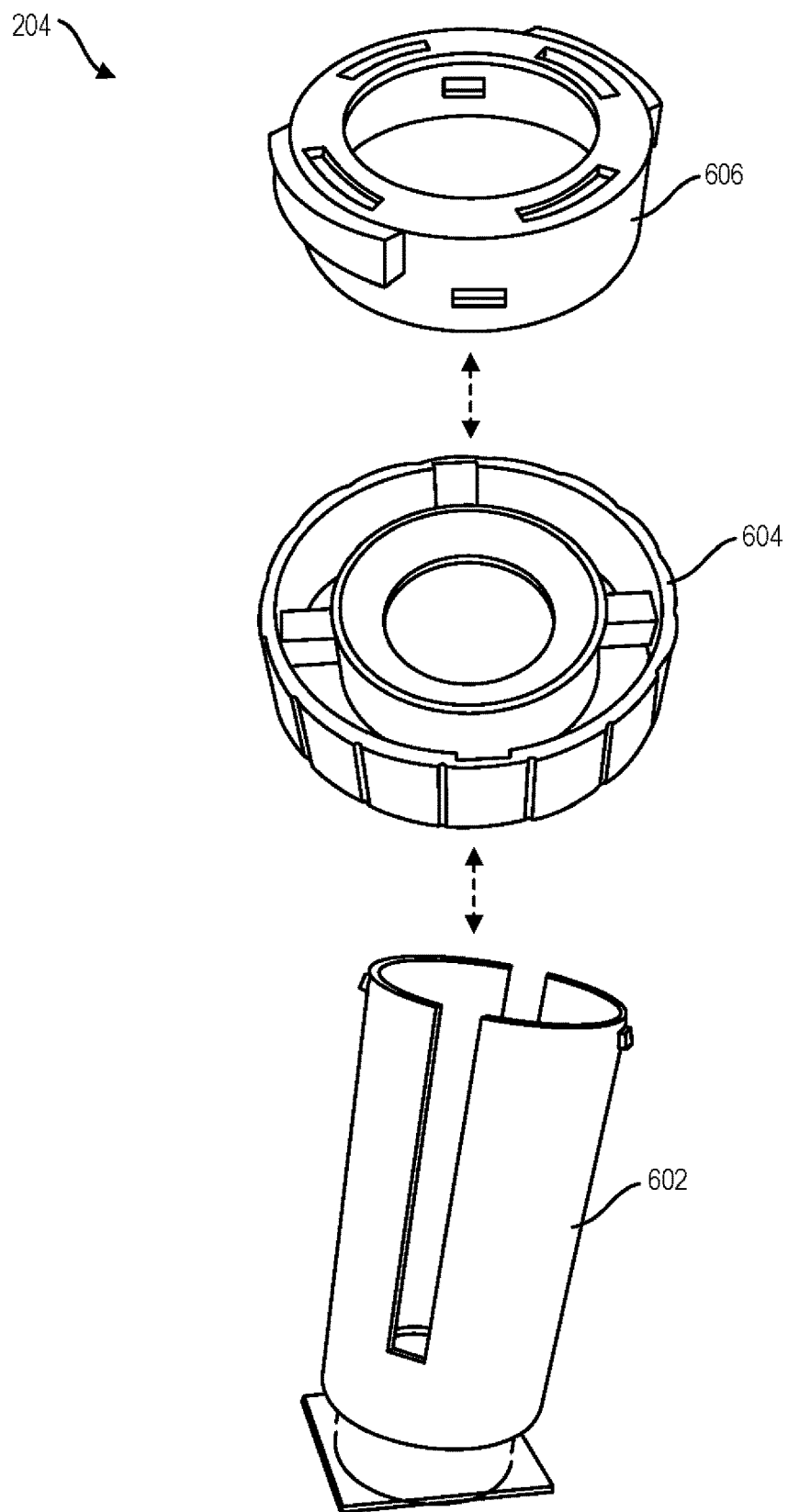
FIG. 6 illustrates a lens-holder configured to hold one or more lenses, in accordance with some implementations of the current subject matter.

FIG. 6 illustrates a lens-holder 204 configured to hold one or more lenses 108. The lens-holder 204 can be made of polylactic acid (PLA), which is a biodegradable and safe polymer. The lens-holder 204 can have an adjustable lens-case 602, a chamber 604, and a cap 606.

The adjustable lens-case 602 can have a height of 9.597 mm, an outer diameter of 37.242 mm, an internal diameter of 34.499 mm, and a thickness of 2.743 mm. The actual lens holding area within the adjustable lens-case 602 can have a diameter of 23.078 mm, a height of 4.387, and an aperture with a diameter of 15.824 mm.

The chamber 604 can have an outer diameter of 30.938 mm, an internal diameter of 28.316 mm, a height of 66.548 mm, and a thickness of 2.622 mm. The chamber 604 can have a clip length of 4.065 mm to allow for the cap 606 to be attached to or fixed on the chamber 604. The chamber 604 can have indents of 43.180 mm in height to allow for adjustment of the adjustable lens-case 602. The chamber 604 can have a base length of 25.399 mm and width 29.971 mm.

The cap 606 can have an outer diameter of 33.515 mm, an internal diameter of 30.937 mm, a height of 10.293 mm, a thickness of 2.578 mm, and an aperture diameter of 23.493 mm.

Figure 7:
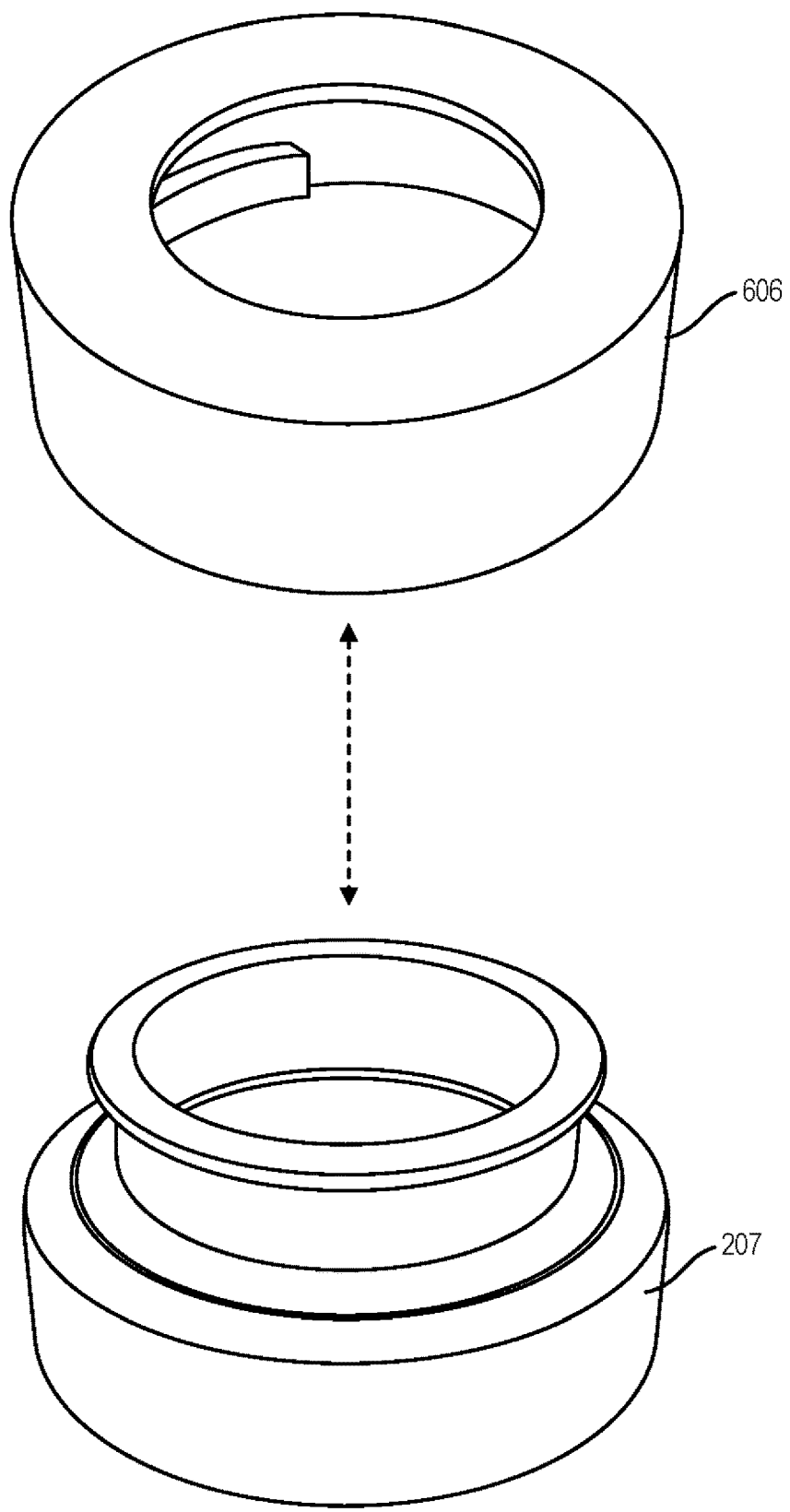
FIG. 7 illustrates an ear-piece holder configured to hold the otoscope head, in accordance with some implementations of the current subject matter.

FIG. 7 illustrates an ear-piece holder 207 configured to hold the otoscope head 208. The ear-piece holder 207 can be made of polylactic acid (PLA), which is a safe biodegradable polymer. The ear-piece holder 207 can have a height of 13.624 mm, an internal diameter of 36.576 mm, a thickness of 2.622 mm and an aperture of 22.860 mm. The ear-piece holder 207 can have an attachment feature that can allow it to be securely attached or fixed to the cap 606 of the lens-holder 204.

Figure 8:
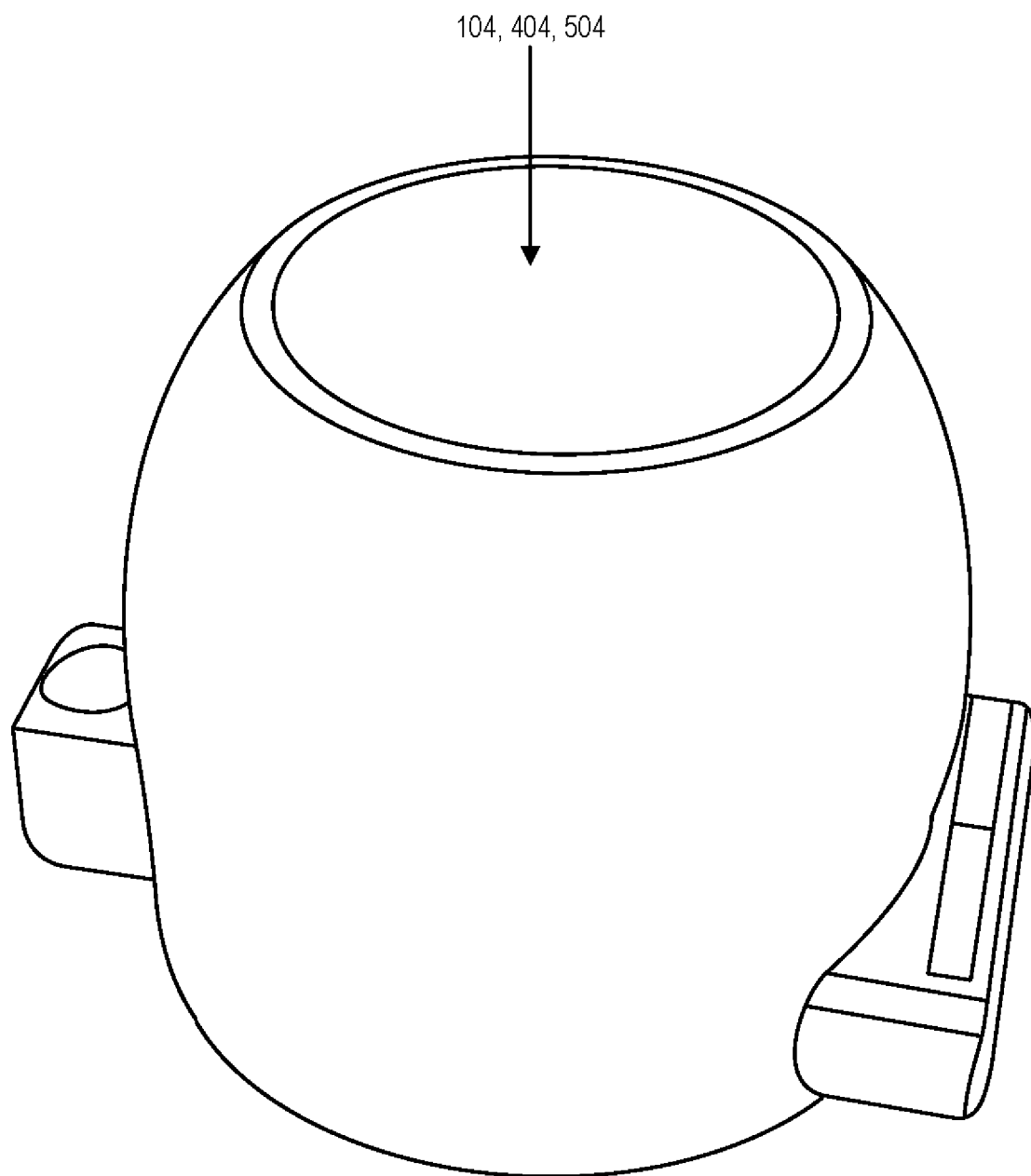
FIG. 8 illustrates one example of the dermascope probe or the dental scope probe, in accordance with some implementations of the current subject matter.

FIG. 8 illustrates one example of the dermascope probe 404 or the dental scope probe 504. The probe 404/504 can be made of polylactic acid (PLA), which is a safe biodegradable polymer.

Figure 9:
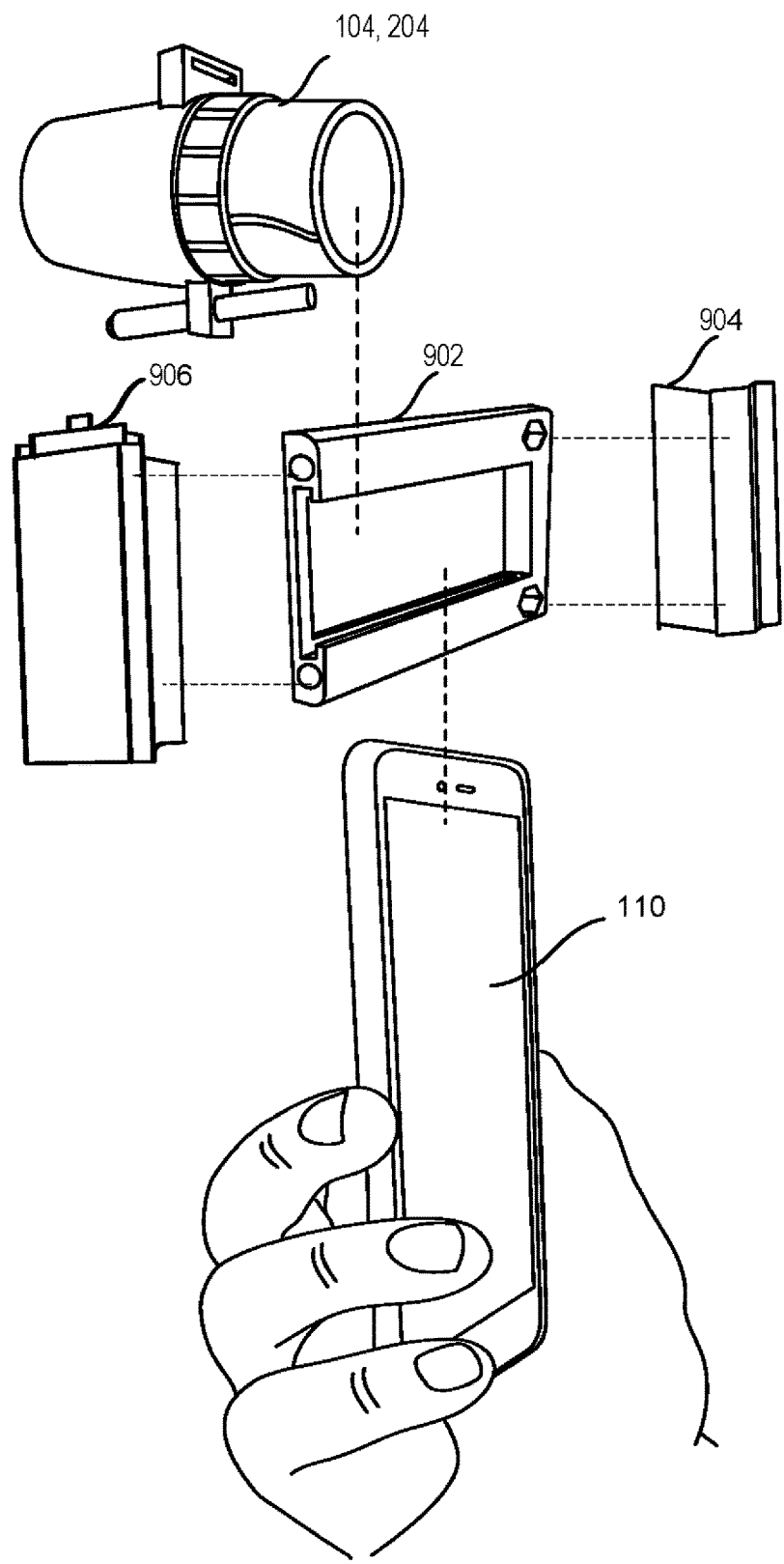
FIG. 9 illustrates an expanded view of the device, which includes a probe, a lens-holder, a mobile device, and a gripper part, in accordance with some implementations of the current subject matter.

FIG. 9 illustrates an expanded view of the device 102, which can include a probe 104, a lens-holder 204, a mobile device 110, and a gripper part 212. The gripper part 212 can include a center part 902, a fixed clamping part 904 configured to be fixed (i.e., non-movable), and an adjustable clamping part 906 configured to be movable or adjustable.

The center part 902 can have brackets 908, which can allow the combination of lens-holder 204 and probe 104 to slide along until the positioning of the lens 108 is adjusted according to the location of the camera 112 on the mobile device 110. Once the positioning of the lens 108 is adjusted, all the parts of the device 102 can be secured so as to prevent any loosening during examination using the device 102.

The center part 902 can have an external width of 57.150 mm, an external height of 48.26 mm, thickness of 5.079 mm, an internal width of 52.070 mm, and an internal height of 25.400 mm. The center part 902 can have a protrusion of length 25.4 mm that can allow for the adjustable clamping part 906 to be adjusted.

The fixed clamping part 904 can have a height of 48 mm, a width of 8 mm, and a clamping curve width of 7.7 mm, which can close-off the opening through which the combination of lens-holder 204 and probe 104 can be inserted into the center part 902. The adjustable clamping part 906 can also have a clamping curvature width of 7.7 mm. Such clamping curvature widths of the fixed clamping part 904 and the adjustable clamping part 906 can securely attach the combination of lens-holder 204 and probe 104 to most modern mobile phones, any one of which can be used as the mobile device 110.

The adjustable clamping part 906 can be moved to increase or decrease the width of the adjustable lens bracket to complement the width of the mobile device 110 being used. The adjustable clamping part 906 can have a height of 60.96 mm, width of 13.97 mm, and a clamping curve width of 7.7 mm. The adjustable clamping part 906 can include clips to allow for adjustment of total gripper width, and the clips can have a width of 27.94 mm.

The adjustable clamping part 906 can also include a hollow opening to insert a battery that can power the combination of lens-holder 204 and probe 104. The hollow opening can have an internal width of 11.43 mm and an internal length of 19.05 mm. The hollow opening can additionally include a charging circuit for that battery. The charging circuit and the batter can be held in place using lid having a width of 13.97 mm and a length of 21.59 mm. The lid can be secured so that the power unit is firmly enclosed.

Figure 10:
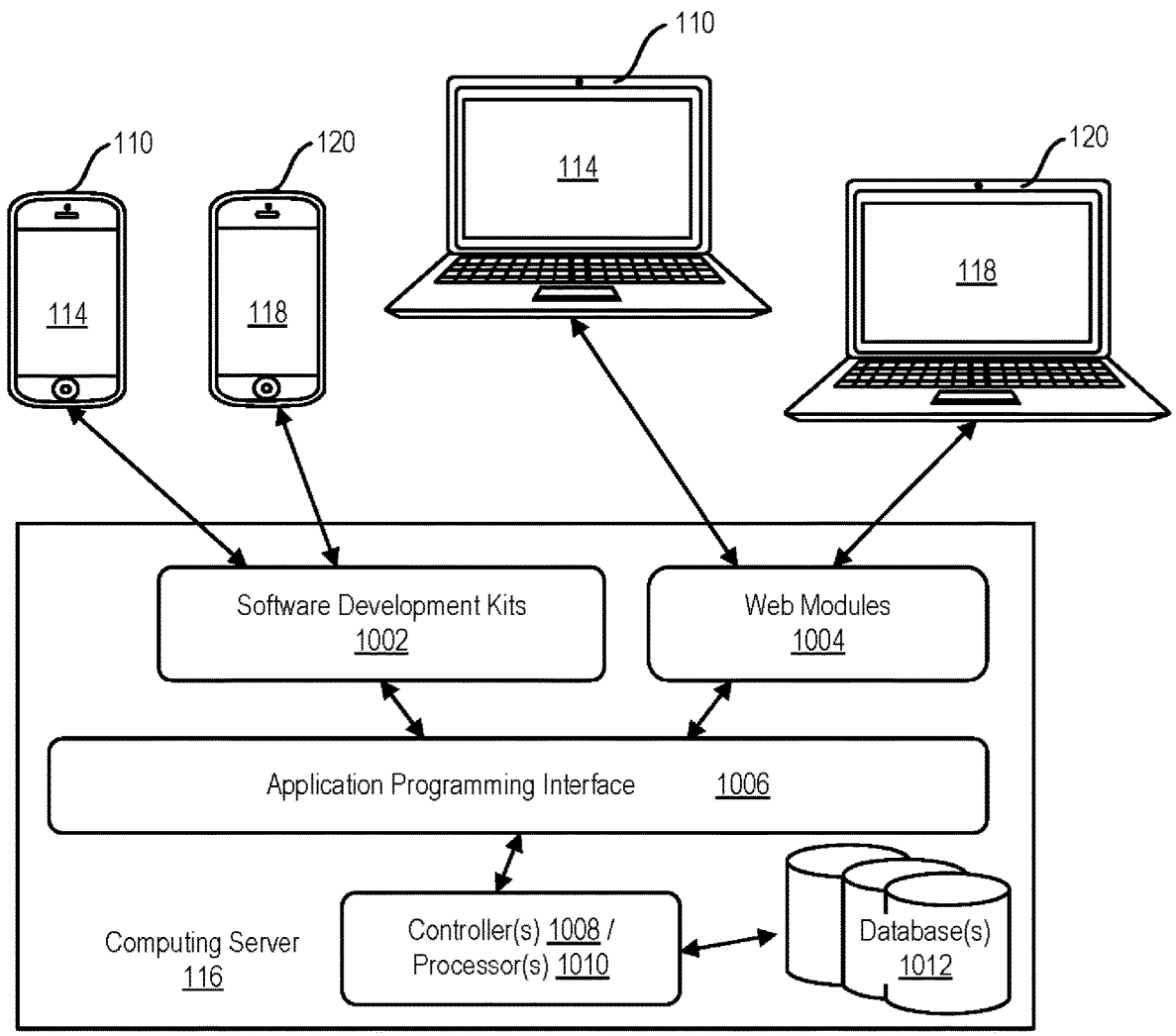
FIG. 10 illustrates one example of the computing server, in accordance with some implementations of the current subject matter.

FIG. 10 illustrates one example of the computing server 116. The computing server 116 can be a cloud computing server. The cloud computing server 116 can include software development kits (SDKs) 1002, web modules 1004, an application programming interface (API) 1006, one or more controllers 1008 including one or more processors 1010, and one or more databases 1012 connected to the one or more controllers 1008. At least one of the one or more SDKs 1002 and the one or more web modules 1004 can receive, from the patient-application 114 on the mobile device 110, images captured (e.g., clicked) by the camera 112 while using the patient-application 114. The one or more SDKs 1002 can receive the images from the patient-application 114 when the mobile device 110 is a mobile phone, a tablet computer, or a phablet computer. The one or more web modules 1004 can receive the images from the patient-application 114 when the mobile device 110 is a laptop computer.

The API 1006 can be a set of subroutine definitions, protocols, and/or tools that define method of communication between the patient-application 114 and the computing server 116 and between the client-application 118 and the computing server 116. The API 1006 can ensure, for example, that the data from the at least one of the one or more software development kits 1002 and the one or more web modules 1004 can be read by the one or more controllers 1008 and the one or more processors 1010.

Each database 1012 can be a cloud database, which can advantageously permit an easy scalability of the database 1012 when required (e.g., when additional data needs to be stored, which can happen, for example, when the number of patients increase beyond a threshold value). In one implementation, access to that database 1012 can be provided as a service. In some implementations, the database 1012 can be run on virtual machine instances. In one implementation, the database 1012 can be a disk storage. In some alternate implementations, the database 1012 can be a main memory (e.g., random access memory) rather than a disk storage. In those alternate implementations, access of data from the main memory can advantageously eliminate seek time when querying the data, which can provides a faster access of data, as compared to accessing data from the disk.

The use of a cloud computing server 116 can be advantageous over a traditional server, as the cloud computing server 116 permits a quick scalability by addition of additional web services within in a few seconds. When the load on the patient-application 114 or clinician-application 118 increases, additional processors 1010 or databases 1012 can be added—or alternately the processing abilities of the existing processors 1010 or databases 1012 can be enhanced—within a few seconds. Additionally, inclusion of all of the one or more software development kits 1002, one or more web modules 1004, API 1006, at least one data processor 1010, and database 1012 within the cloud computing server 116 can advantageously enable: a dynamic provisioning, monitoring and managing of the patient-application 114 and clinician-application 118; as well as an easy and a quick (e.g., within a few seconds) restoring the patient-application 114 and/or the clinician-application 118 to a previous version of those applications if and when required.

Figure 11:
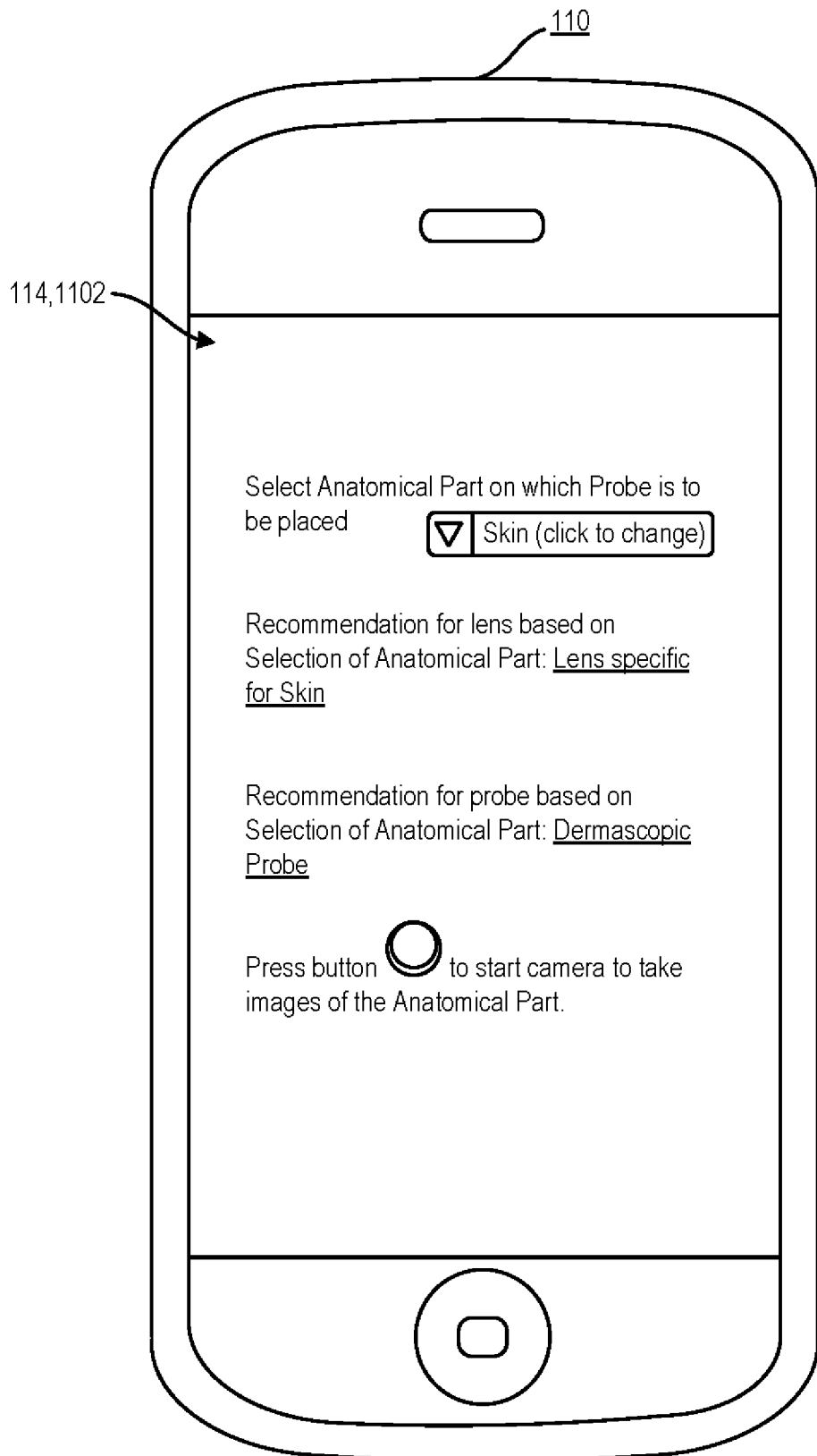
FIG. 11 illustrates one example of a graphical user interface of the patient-application to calibrate the mobile device, in accordance with some implementations of the current subject matter.

FIG. 11 illustrates one example of a graphical user interface 1102 of the patient-application 114 to calibrate the mobile device 110. The graphical user interface 1102 can display a drop-down menu to prompt the user to select an anatomical part—from several anatomical parts, including an ear, a nose, an eye, a mouth, teeth, skin, and/or the like—on which the probe 104 is to be placed. This ensures that the calibration is specific to the selected anatomical part. When the user selects a particular anatomical part (e.g., skin), the patient-application 114 can optionally determine and display, on the graphical user interface 1102, recommendations for lens as well as the probe 104 for the anatomical part. The graphical user interface 1102 can display a button, which when pressed, can activate the camera of the mobile device 110 to take images of the anatomical part and subsequently generate parameters for filters to be later used to edit images, as described in greater detail below by FIGS. 12 and 13.

Figure 12:
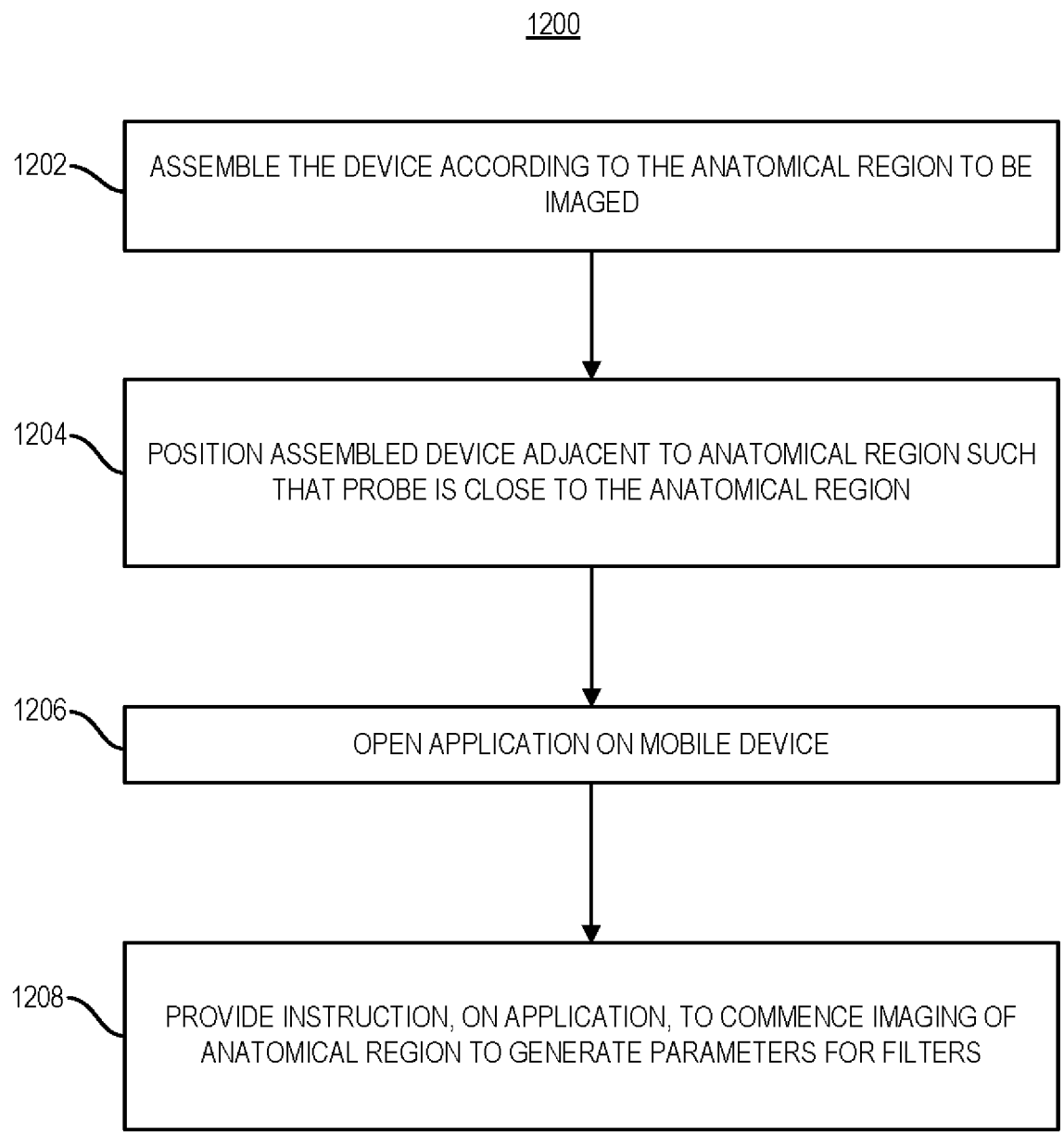
FIG. 12 illustrates a method performed by a user to calibrate the mobile device to generate parameters for filters to be invoked later by a user, in accordance with some implementations of the current subject matter.

FIG. 12 illustrates a method 1200 performed by a user to calibrate the mobile device 110 to generate parameters for filters to be invoked later by a user. The user can assemble, at 1202, the device 102 according to the anatomical region to be used. The assembly of the device 102 can include attaching or mating the components of the device 102 so that the device 102 can image a patient 106, and then send filtered and approved version of that image to a clinician-application 118. The assembly can include selecting a lens and/or a probe of the device 102 that are specific to the anatomical region. The user can position, at 1204, the assembled device adjacent to the anatomical region of the patient 106 such that the probe is close to (e.g., either in the vicinity of or touching, as may be medically recommended) that anatomical region. The anatomical region can be an ear, a nose, an eye, a mouth, teeth, skin, and/or the like. The user can open (e.g., click an icon on the home screen of the mobile device 110 to run), at 1206, the patient-application 114 on the mobile device 110.

The user can provide, at 1208, an instruction on the patient-application 114 (e.g., by pressing/clicking a button) to commence imaging of the anatomical region to generate parameters for filters. More specifically, the patient-application 114 can run a specific programming function, which when run can return a value that is referred to as the parameter. For example: the execution of a morphological operation on the image can return a value referred to as parameter M; the execution of a histogram equalization function on the image can return a value referred to as parameter H; the execution of a noise removal function can return a value referred to as parameter N; the execution of a contrast adjustment function on the image can return a value referred to as parameter C; the execution of an unsharp masking function can return a value referred to as a parameter U; and the like. Each of the values or parameters M, H, N, C, U, and/or the like can be a data structure, such as a matrix. The parameters M, H, N, C, U, and/or the like can be stored in the one or more databases 1214.

Figure 13:
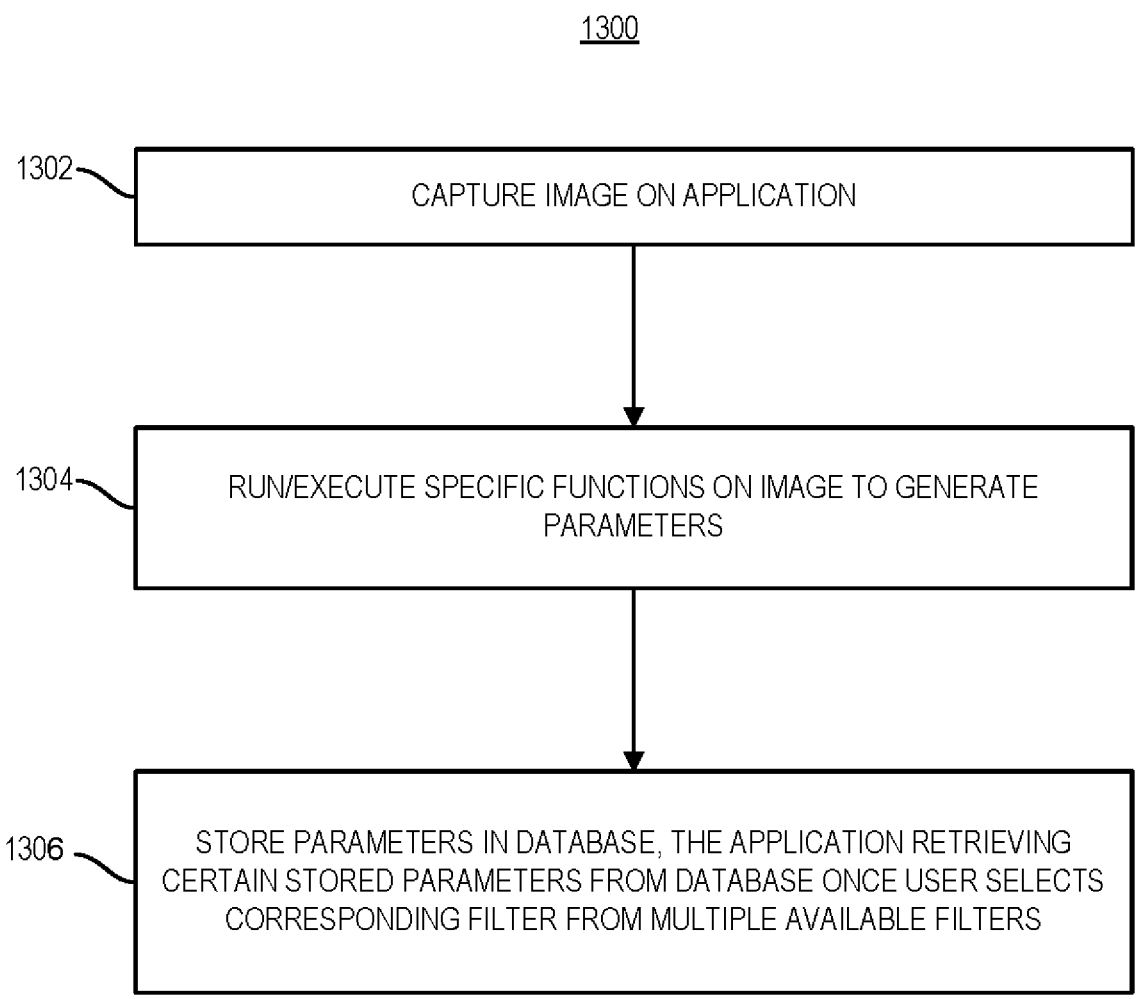
FIG. 13 illustrates a method performed by the mobile device and the server to generate parameters for filters to be invoked later by a user, in accordance with some implementations of the current subject matter.

FIG. 13 illustrates a method 1300 performed by the mobile device 110 and the server 116 to generate parameters for filters to be invoked later by a user. The user invoking the parameters at a later time may or may not be the same as the user performing the steps 1202, 1204, 1206, and 1208. The patient-application 114 can use a camera of the mobile device 110 to capture (e.g., click), at 1302, an image of the anatomical part on the patient-application 114. In some implementations, at least one processor of the mobile device 110 may capture the image in response to a manual instruction by a user of the mobile device 110. In other implementations, at least one processor of the mobile device 110 may capture the image in response to an automatic instruction by the one or more processors 1010.

The one or more processors 1010 can run or execute, at 1304, specific functions to generate corresponding parameters. For example: the execution of a morphological operation on the image can return a value referred to as parameter M; the execution of a histogram equalization function on the image can return a value referred to as parameter H; the execution of a noise removal function can return a value referred to as parameter N; the execution of a contrast adjustment function on the image can return a value referred to as parameter C; the execution of an unsharp masking function can return a value referred to as a parameter U; and the like. Each of the values or parameters M, H, N, C, U, and/or the like can be a data structure, such as a matrix. While the execution of the specific functions at 1304 is described as being performed by the one or more processors 1010, in alternate implementations the one or more processors 1010 can provide an instruction to at least one processor of the mobile device 110 to perform this execution.

The one or more databases 1014 can store, at 1306, the parameters M, H, N, C, U, and/or the like. The patient-application 114 can retrieve one or more of the stored parameters from the one or more databases 1014 when a user selects a filter associated with those one or more parameters from a plurality of filters. While the parameters M, H, N, C, U, and/or the like are described as being stored in the one or more databases 1014, in alternate implementations the one or more processors 1010 can instruct at least one processor of the mobile device 110 to store those parameters in a main memory of the mobile device 110, wherein the main memory subsequently can store those parameters.

The calibrated mobile device 110 can capture high quality images, which can be medical grade images. Medical grade images can include optimal values of at least the following: contrast, blur, noise, artifacts, and distortion. The optimal contrast can ensure visibility of various anatomical portions of the anatomical part. The optimal blur can blur the anatomical portions, of the anatomical part, that may not be important or may be irrelevant for analyzing the anatomical part. The optimal noise may cause optimal visibility of relevant anatomical portions of the anatomical part. The effect of the noise can be most significant on the low-contrast portions of the image. The optimal distortion can optimize the size, shape, and relative positions of various anatomical portions of the anatomical part.

Figure 14:
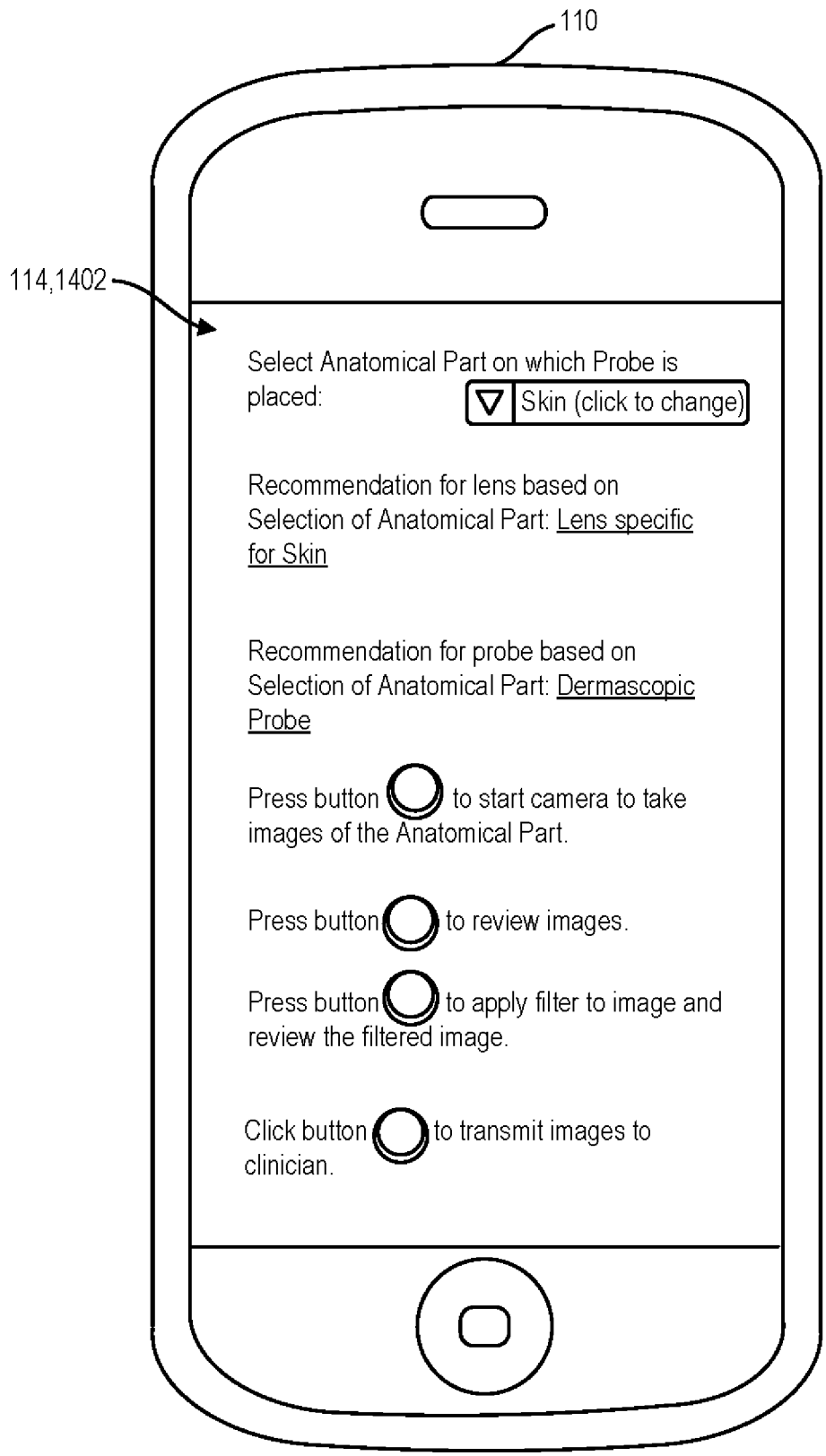
FIG. 14 illustrates one example of a graphical user interface of the patient-application to be used after the device has been calibrated according to FIGS. 11-13, in accordance with some implementations of the current subject matter.

FIG. 14 illustrates one example of a graphical user interface 1402 of the patient-application 114 to be used after the device 102 has been calibrated according to FIGS. 11-13. The graphical user interface 1402 can display a drop-down menu to prompt the user to select an anatomical part—from several anatomical parts, including an ear, a nose, an eye, a mouth, teeth, skin, and/or the like—on which the probe 104 is to be placed. When the user selects a particular anatomical part (e.g., Skin), the patient-application 114 can optionally display, on the graphical user interface 1402, recommendations for lens as well as the probe 104 for the anatomical part. The graphical user interface 1402 can display: a first button, which when pressed, can activate the camera of the mobile device 110; a second button, which when pressed, can display the images clicked using the camera; a third button, which when pressed, can enable a user to apply a filter to the image (which results in the patient-application 114 retrieving the corresponding parameters retrieved from the database to run the programing code for the filter function) and then review the filtered image; and a fourth button, which when pressed, can transmit the images to an clinician-application 118 executed on the clinical computer 120.

Figure 15:
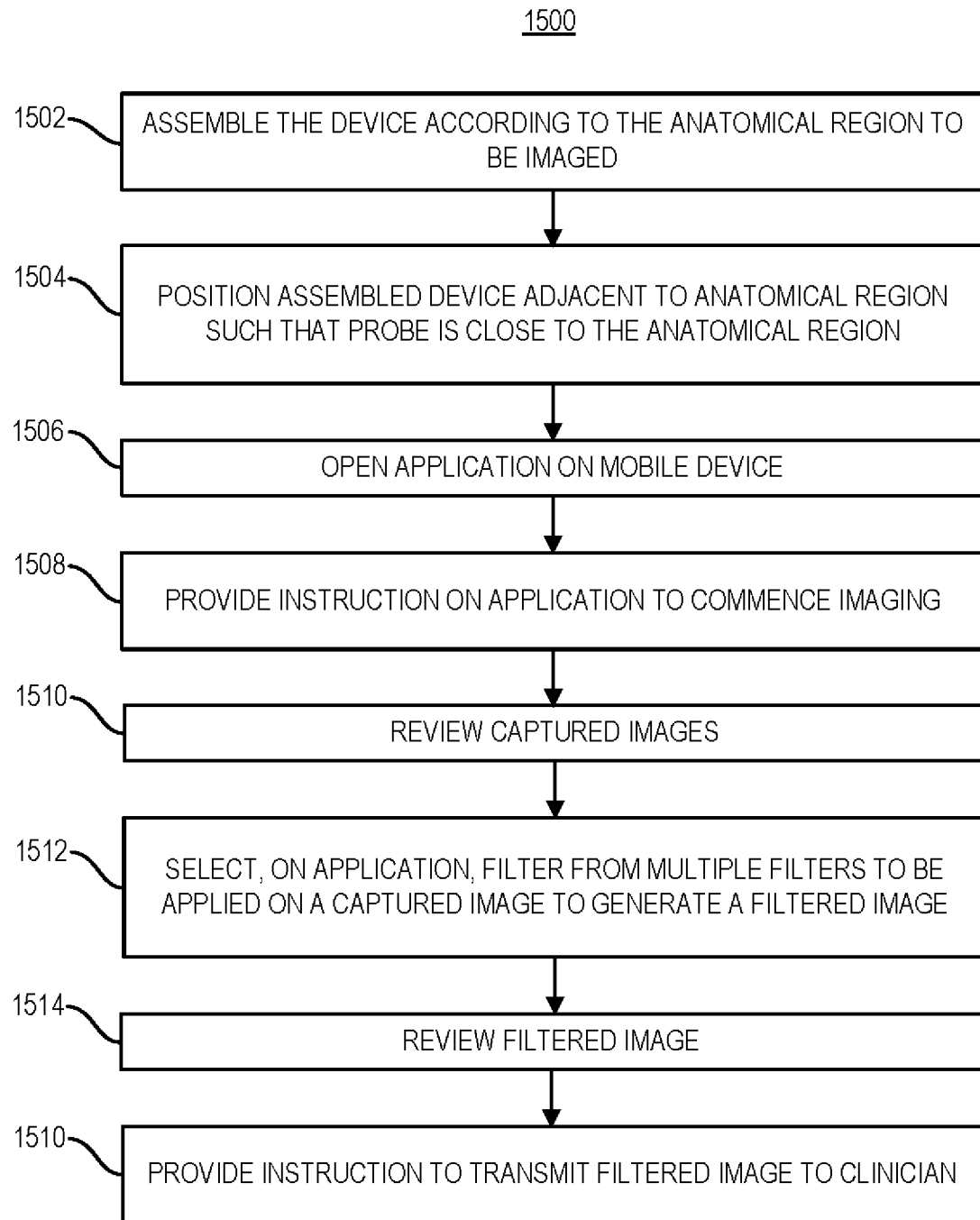
FIG. 15 illustrates a method of using the calibrated device by a user, in accordance with some implementations of the current subject matter.

FIG. 15 illustrates a method 1500 of using the calibrated device 102 by a user. The user using the calibrated device 102 may be different than the user calibrating the device 102 by performing the steps 1202, 1204, 1206, and 1208. For example, the user using the calibrated device 102 may be a patient, and the user calibrating the device 102 may be a technician or a seller of the device. The user can assemble, at 1502, the device according to the anatomical region to be imaged. The anatomical region can be an ear, a nose, an eye, a mouth, teeth, skin, and/or the like. The assembly of the device 102 can include attaching or mating the components of the device 102 so that the device 102 can image a patient 106, and then send filtered and approved version of that image to a clinician-application 118. The assembly of the device 102 can also include selecting a lens and/or a probe of the device 102 that are specific to the anatomical region.

The user can position, at 1504, the assembled device adjacent to the anatomical region of the patient 106 such that the probe is close to (e.g., either in the vicinity of or touching, as may be medically recommended) that anatomical region. The anatomical region can be an ear, a nose, an eye, a mouth, teeth, skin, and/or the like. The user can open (e.g., click an icon on the home screen of the mobile device 110 to run), at 1506, the patient-application 114 on the mobile device 110. The user can provide, at 1508, an instruction on the patient-application 114 (e.g., by pressing/ clicking a button) to commence imaging of the anatomical region. Once the images are captured, the user can review, at 1510, the images on the patient-application 114.

The user can select, at 1512 and on the patient-application 114, a filter, from multiple filters, to be applied on a captured image to generate a filtered image. More particularly, the patient-application 114 can retrieve the stored parameters M, H, N, C, U, and/or the like—that are specific to or associated with the selected filter—from the one or more databases 1012, and then execute the programming code for the selected filter by using the retrieved parameters to generate a filtered image. The user can review, at 1514, the filtered image on the patient-application 114. The user can provide, at 1510, an instruction on the patient-application 114 to transmit the filtered image to the clinician-application 118.

Figure 16:
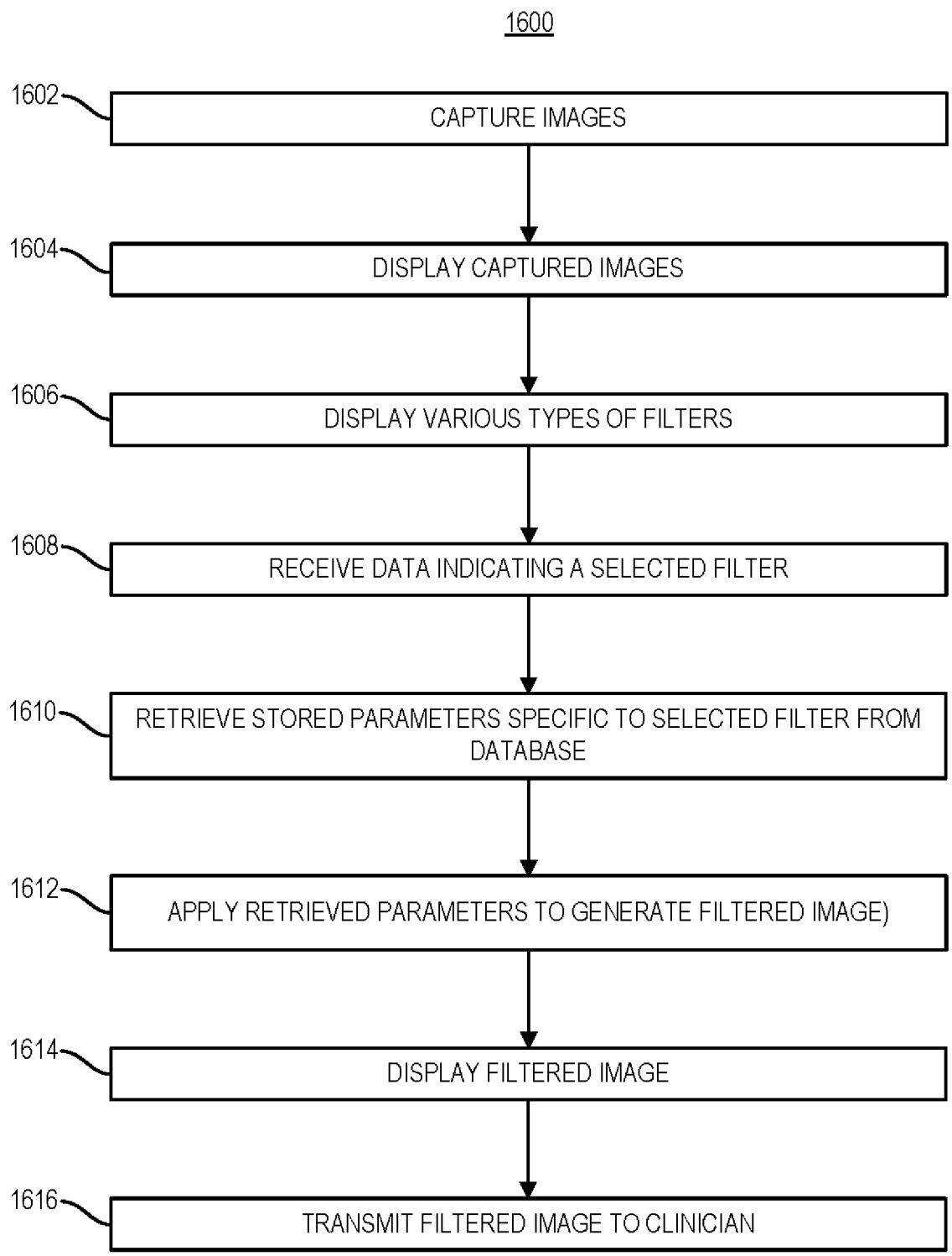
FIG. 16 illustrates a method performed by the patient-application and the server to capture images of a patient, modify those images in accordance with selection by a user, and transmit those images to a clinician-application, in accordance with some implementations of the current subject matter.

FIG. 16 illustrates a method 1600 performed by the patient-application 114 and the server 116 to capture images of a patient 106, modify those images in accordance with selection by a user, and transmit those images to a clinician-application 118. The patient-application 114 can use a camera of the mobile device 110 to capture, at 1602, images of an anatomical region of a patient 106. The patient-application 114 can display, at 1604 the captured images on a graphical user interface 1402. The display on the graphical user interface 1402 can be controlled by the one or more controllers 1008.

The patient-application 114 can display, at 1606, types of filters on the graphical user interface 1402. The one or more processors 1010 can receive, at 1608, data indicating a filter selected by a user from the various types of filters. The one or more processors 1010 can retrieve the stored parameters (e.g., M, H, N, C, U, and/or the like) that are specific to or associated with the selected filter. The one or more processors 1012 can apply, at 1612, the retrieved parameters to the programming code of the selected filter to generate a filtered image. The graphical user interface 1402 can display, at 1614, the filtered image. The patient-application 114 can transmit, at 1616, the filtered image to the clinician-application 118.

Figure 17:
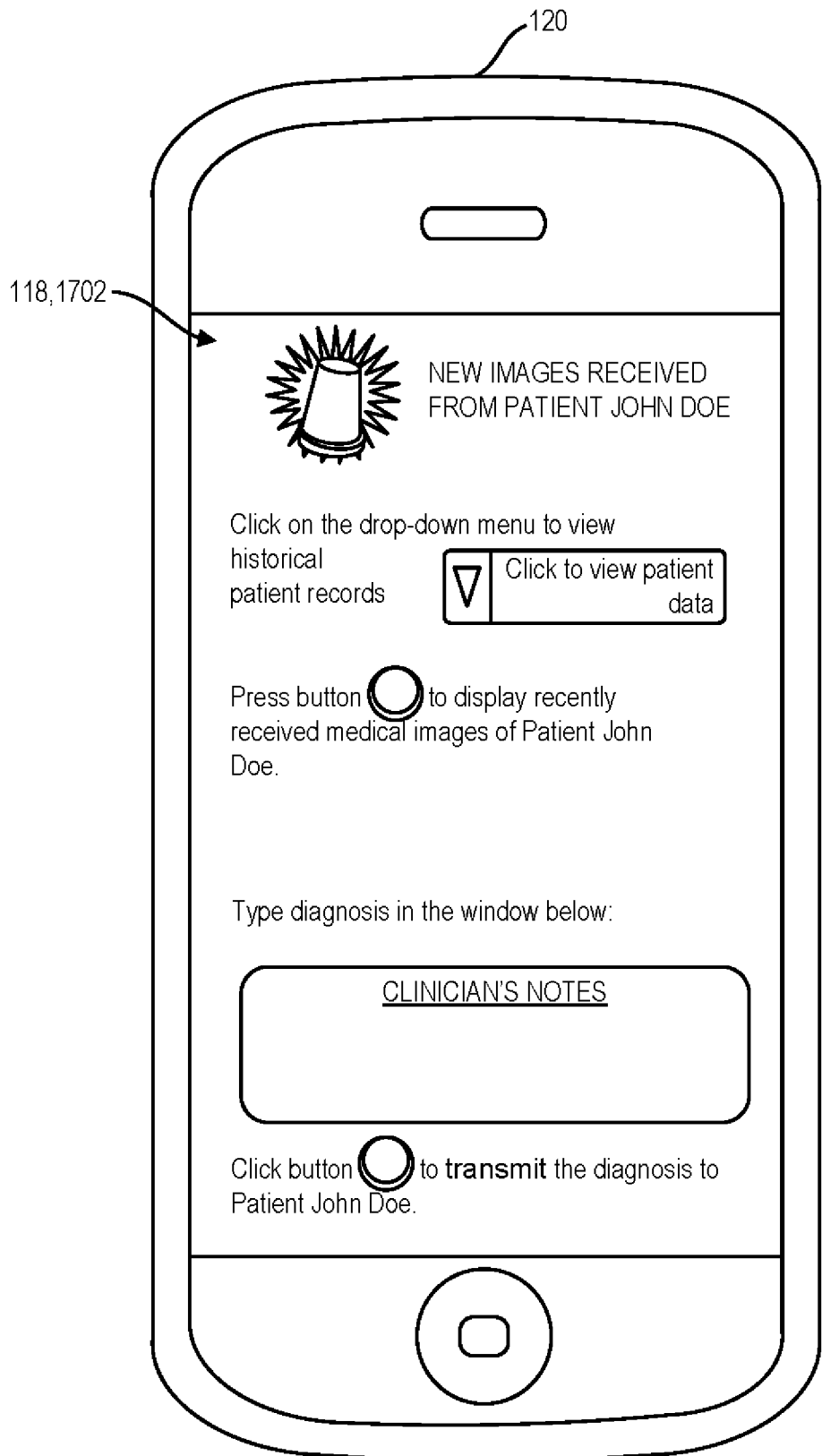
FIG. 17 illustrates one example of a graphical user interface of the clinician-application executed on the clinical computer, in accordance with some implementations of the current subject matter.

FIG. 17 illustrates one example of a graphical user interface 1702 of the clinician-application 118 executed on the clinical computer 120. When the patient-application 114 transmits the images to the clinician-application 118, the clinician-application 118 can generate an alarm on the graphical user interface 1702 to indicate to a user (e.g., clinician) that new images have been received from the user of the patient-application 114 (e.g., patient John Doe). The graphical user interface 1702 can include a drop-down menu, which, when selected by the clinician, can display historical records of the patient. The graphical user interface 1702 can further include a button, which, when pressed by the clinician can display the recently viewed medical images of the patient. The graphical user interface 1702 can provide an area where the clinician can input diagnosis of the patient based on the images. The graphical user interface 1702 can include another button, which, when pressed by the clinician, can transmit the diagnosis to the patient-application 114.

Figure 18:
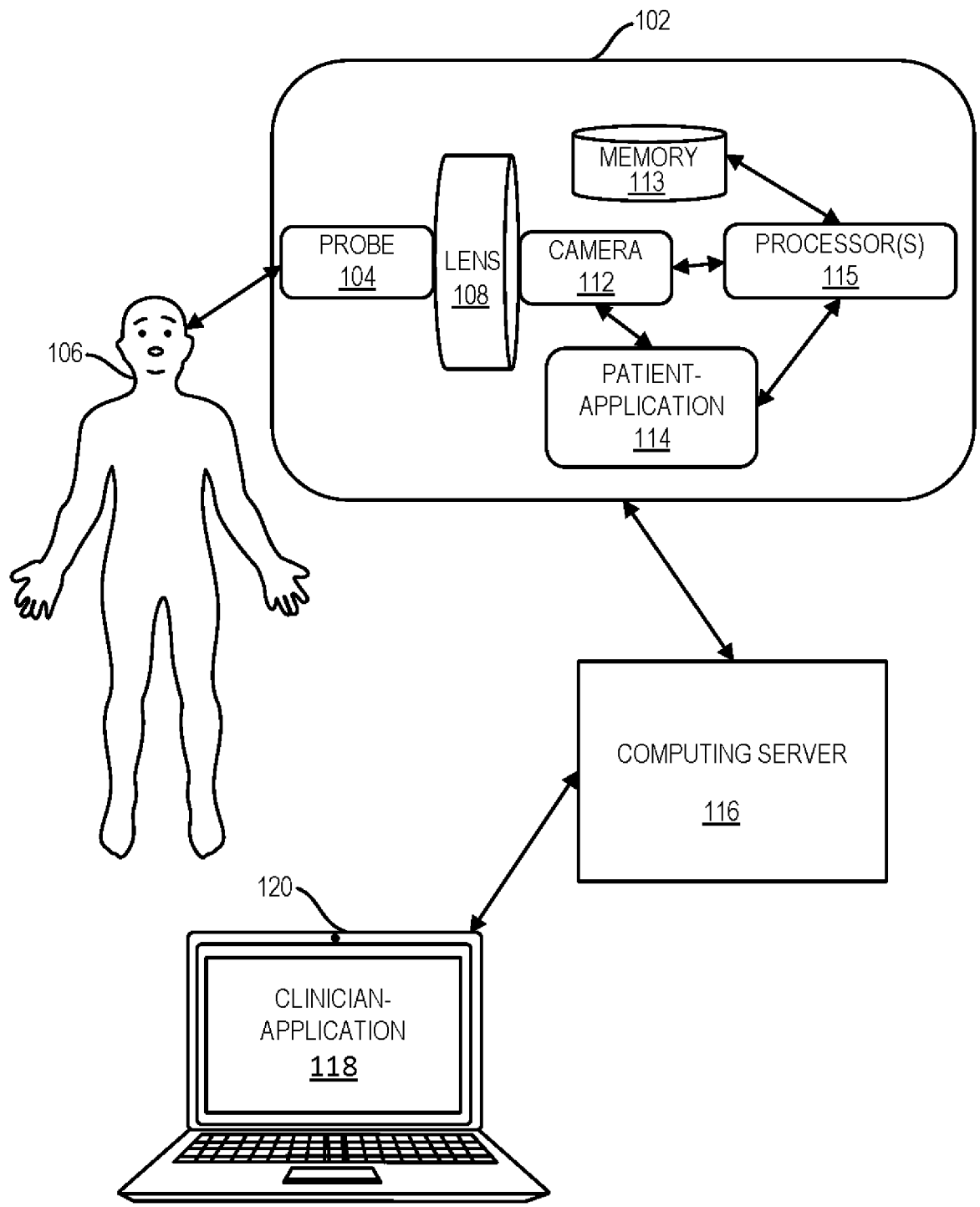
FIG. 18 illustrates an alternative device where the camera, patient-application, memory and the processor/controller are directly a part of the device, rather than being a part of a separate mobile device as is the case in the implementation of FIG. 1, in accordance with some implementations of the current subject matter.

FIG. 18 illustrates an alternative device 102 where the camera 112, patient-application 114, memory 113 and the processor/controller 115 are directly a part of the device 102, rather than being a part of a separate mobile device 110 as is the case in the implementation of FIG. 1. That is, the device 102 may not need a mobile device 110, such as a mobile phone, to perform the functionality described by FIG. 1.

Various implementations of the subject matter described herein can be realized/implemented in digital electronic circuitry, integrated circuitry, specially designed application specific integrated circuits (ASICs), computer hardware, firmware, software, and/or combinations thereof. These various implementations can be implemented in one or more computer programs. These computer programs can be executable and/or interpreted on a programmable system. The programmable system can include at least one programmable processor, which can have a special purpose or a general purpose. The at least one programmable processor can be coupled to a storage system, at least one input device, and at least one output device. The at least one programmable processor can receive data and instructions from, and can transmit data and instructions to, the storage system, the at least one input device, and the at least one output device.

These computer programs (also known as programs, software, software applications or code) can include machine instructions for a programmable processor, and can be implemented in a high-level procedural and/or object-oriented programming language, and/or in assembly/machine language. As can be used herein, the term "machine-readable medium" can refer to any computer program product, apparatus and/or device (for example, magnetic discs, optical disks, memory, programmable logic devices (PLDs)) used to provide machine instructions and/or data to a programmable processor, including a machine-readable medium that can receive machine instructions as a machine-readable signal. The term "machine-readable signal" can refer to any signal used to provide machine instructions and/or data to a programmable processor.

To provide for interaction with a user, the subject matter described herein can be implemented on a computer that can display data to one or more users on a display device, such as a cathode ray tube (CRT) device, a liquid crystal display (LCD) monitor, a light emitting diode (LED) monitor, or any other display device. The computer can receive data from the one or more users via a keyboard, a mouse, a trackball, a joystick, or any other input device. To provide for interaction with the user, other devices can also be provided, such as devices operating based on user feedback, which can include sensory feedback, such as visual feedback, auditory feedback, tactile feedback, and any other feedback. The input from the user can be received in any form, such as acoustic input, speech input, tactile input, or any other input.

The subject matter described herein can be implemented in a computing system that can include at least one of a back-end component, a middleware component, a front-end component, and one or more combinations thereof. The back-end component can be a data server. The middleware component can be an application server. The front-end component can be a client computer having a graphical user interface or a web browser, through which a user can interact with an implementation of the subject matter described herein. The components of the system can be interconnected by any form or medium of digital data communication, such as a communication network. Examples of communication networks can include a local area network, a wide area network, internet, intranet, BLUETOOTH network, infrared network, or other networks.

Although a few variations have been described in detail above, other modifications can be possible. For example, the logic flows depicted in the accompanying figures and described herein do not require the particular order shown, or sequential order, to achieve desirable results. Additionally, dimensions of various components have been provided. These dimensions are examples, and alternates for each dimension may be possible. For example, in other implementations, each dimension may have an alternative value that can range from minus ten percent (i.e., −10%) of that dimension to plus ten percent (i.e., +10%) of that dimension. Additionally, dimensions of each component can be scaled up or down to ensure a proper fit of that component with any other element/component, such as the mobile device 110, probe 104, the lens-holder 204, or any other element/component.

Other embodiments may be within the scope of the following claims.

What is claimed is:
1. A system comprising:
   an application installed on a mobile device to:
      display a plurality of filters;
      receive a selection of at least one filter of the plurality of filters; and
   at least one controller to:
      receive a prior image of an anatomical region;
      execute one or more functions on the prior image to return a plurality of parameters for the mobile device;
      receive, from the application, the selection of the at least one filter;
      identify at least one parameter of the plurality of parameters obtained during a calibration of the mobile device;
      execute the at least one filter on an image of the anatomical region of a body by using the at least one parameter to generate a filtered image; and
      transmit the filtered image to another application.

2. The system of claim 1, further comprising:
a camera to:
    generate the image in response to activation of the camera being located within a preset distance from the anatomical region.

3. The system of claim 2, further comprising:
at least one lens to be positioned between the camera and the anatomical region.

4. The system of claim 1, wherein:
the anatomical region is of a patient;
the application is configured to be accessed by the patient; and
the other application is configured to be accessed by a clinician.

5. The system of claim 1, wherein the application and the at least one controller are a part of an anatomical-imaging device.

6. The system of claim 1, wherein the application and the other application are controlled by a server, wherein the application is a part of an anatomical-imaging device coupled to the server by way of a communication network, wherein the at least one controller is a part of the server.

7. The system of claim 6, wherein the server is a cloud computing server.

8. The system of claim 1, wherein the one or more functions comprise one or more of a histogram equalization function on the prior image, a noise removal function on the prior image, a contrast adjustment function on the prior image, an unsharp masking function on the prior image.

9. The system of claim 1, wherein the anatomical region comprises at least a portion of one or more of an ear, a nose, an eye, a mouth, teeth, or skin.

10. A device comprising:
a probe to inspect an anatomical region of a body; and
at least one lens to allow light to pass from the inspected anatomical region to a mobile device, wherein the mobile device comprises:
    an application to:
        display a plurality of filters;
        receive a selection of at least one filter of the plurality of filters; and
    at least one controller to:
        receive a prior image of the anatomical region;
        execute one or more functions on the prior image to return a plurality of parameters for the mobile device;
        receive, from the application, the selection of the at least one filter;
        identify at least one parameter of the plurality of parameters obtained during a calibration of the mobile device;
        execute the at least one filter on an image of the anatomical region by using the at least one parameter to generate a filtered image; and
        transmit the filtered image to another application.

11. The device of claim 10, further comprising:
an adjustable gripper apparatus to be adjusted according to dimensions of the mobile device to grip the mobile device.

12. The device of claim 11, wherein the adjustable gripper apparatus comprises a fixed clamping apparatus and a movable clamping apparatus to be moved to grip the mobile device.

13. The device of claim 12, wherein the movable clamping apparatus comprises an opening for a battery that provides electric power to the probe.

14. The device of claim 10, wherein the mobile device comprises:
a camera to:
    generate the image in response to activation of the camera being located within a preset distance from the anatomical region.

15. The device of claim 10, wherein:
the anatomical region is of a patient;
the application is configured to be accessed by the patient; and
the other application is configured to be accessed by a clinician.

16. The device of claim 10, wherein the application and the other application are controlled by a server, wherein the application is a part of an anatomical-imaging device coupled to the server by way of a communication network, wherein the at least one controller is a part of the server.

17. The device of claim 16, wherein the server is a cloud computing server.

18. The device of claim 10, wherein the anatomical region comprises at least a portion of one or more of an ear, a nose, an eye, a mouth, teeth, or skin.

19. A method comprising:
displaying, by an application installed on a mobile device, a plurality of filters;
receiving, by the application, a selection of at least one filter of the plurality of filters;
receiving, by at least one controller communicatively coupled to the application, a prior image of an anatomical region;
executing, by the at least one controller, one or more functions on the prior image to return a plurality of parameters for the mobile device;
identifying, by the at least one controller, at least one parameter of the plurality of parameters obtained during a calibration of the mobile device;
executing, by the at least one controller, the at least one filter on an image of the anatomical region of a body by using the at least one parameter to generate a filtered image; and
transmitting, by the at least one controller, the filtered image to another application.

* * * * *